(12) United States Patent
Kurihara et al.

(10) Patent No.: US 10,100,008 B2
(45) Date of Patent: Oct. 16, 2018

(54) IMMUNOSTIMULATING AGENT

(71) Applicant: AJINOMOTO CO., INC., Tokyo (JP)

(72) Inventors: Shigekazu Kurihara, Kawasaki (JP); Kenji Tanaka, Kawasaki (JP); Wataru Kurosawa, Kawasaki (JP); Hiroshi Umishio, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/331,094

(22) Filed: Oct. 21, 2016

(65) Prior Publication Data

US 2017/0036999 A1 Feb. 9, 2017

Related U.S. Application Data

(63) Continuation of application No. PCT/JP2015/063155, filed on Apr. 24, 2015.

(30) Foreign Application Priority Data

Apr. 25, 2014 (JP) .................................. 2014/091142
Feb. 27, 2015 (JP) .................................. 2015/039593

(51) Int. Cl.
  C07C 323/52 (2006.01)
  A61K 39/39 (2006.01)
  A61K 39/00 (2006.01)
(52) U.S. Cl.
  CPC ............ C07C 323/52 (2013.01); A61K 39/39 (2013.01); *A61K 2039/55511* (2013.01)
(58) Field of Classification Search
  CPC .......... A61K 2039/55511; A61K 39/39; C07C 323/52
  See application file for complete search history.

(56) References Cited

U.S. PATENT DOCUMENTS

| 5,700,910 A | 12/1997 | Metzger et al. |
| 6,703,031 B1 | 3/2004 | Iwasaki et al. |
| 2014/0065179 A1 | 3/2014 | Nozaki et al. |

FOREIGN PATENT DOCUMENTS

| AU | 611385 B2 | 1/1987 |
| AU | 612130 B2 | 7/1988 |
| CN | 1315940 A | 10/2001 |
| EP | 0 210 412 A2 | 2/1987 |
| EP | 0 463 514 A1 | 1/1992 |
| EP | 0 839 528 A1 | 5/1998 |
| JP | 59-219262 A | 12/1984 |
| JP | 62-63600 A | 3/1987 |
| JP | 63-264444 A | 11/1988 |
| JP | 4-230359 A | 8/1992 |
| JP | 5-186419 A | 7/1993 |
| JP | 5-507705 A | 11/1993 |
| JP | 11-302250 A | 11/1999 |
| WO | WO 91/18594 A1 | 12/1991 |
| WO | WO 96/18600 A1 | 6/1996 |
| WO | WO 99/10008 A1 | 3/1999 |
| WO | WO 01/59067 A2 | 8/2001 |
| WO | WO 02/094764 A1 | 11/2002 |
| WO | WO 03/006007 A1 | 1/2003 |
| WO | WO 2009/142988 A2 | 11/2009 |
| WO | WO 2009/157759 A1 | 12/2009 |
| WO | WO 2009/157767 A1 | 12/2009 |
| WO | WO 2012/124631 A1 | 9/2012 |
| WO | WO 2014/191080 A1 | 12/2014 |
| WO | WO 2015/034924 A1 | 3/2015 |
| WO | WO 2015/059225 A1 | 4/2015 |
| WO | WO 2016/012385 A1 | 1/2016 |

OTHER PUBLICATIONS

Loftsson et al. Cyclodextrins and their pharmaceutical applications. International Journal of Pharmaceutics, 2007. vol. 329, pp. 1-11. (Year: 2007).*
Boecker et al. Design and Synthesis of Thioi-Reactive Lipopeptides. Bioorganic & Medicinal Chemistry Letters, 1998. vol. 8, pp. 2055-2058. (Year: 1998).*
Rasheed et al. Cyclodextrins as Drug Carrier Molecule: A Review . Sci Pharm. 2008; vol. 76, pp. 567-598. (Year: 2008).*
Günther Jung, et al., "The Mitogenic Principle of *Escherichia coli* Lipoprotein: Synthesis, Spectroscopic Characterization, and Mitogenicity of N-Palmitoyl-S-[(2R,S)-2,3-dipalmitoyloxypropyl]-(R)-cysteine Methyl Ester" Liebigs Ann. Chem., 1983, pp. 1608-1622.
Jonathan G. Heath, et al., "Chiral Molecular Recognition in Monolayers of Diastereomeric N-Acylamino Acid Methyl Esters at the Air/Water Interface" J. Am. Chem. Soc., vol. 114, No. 12, 1992, pp. 4500-4514.
International Search Report dated Aug. 26, 2015 in PCT/JP2015/063155 filed Apr. 24, 2015.

(Continued)

*Primary Examiner* — Marcela M Cordero Garcia
(74) *Attorney, Agent, or Firm* — Oblon, McClelland, Maier & Neustadt, L.L.P.

(57) ABSTRACT

Compounds represented by formula (I):

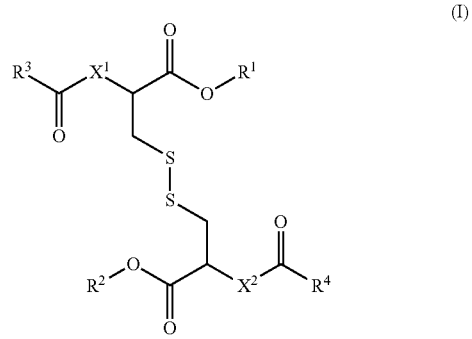

(I)

wherein each symbol is as defined herein, have an immunostimulatory effect and are useful as immunostimulating agents, particularly as adjuvants, and for compositions containing such a compound, and for vaccines containing such a compound and an antigen.

31 Claims, 11 Drawing Sheets

(56) References Cited

OTHER PUBLICATIONS

J. Cybulia, et al., "The mitogenic principle of *Escherichia coli* lipoprotein: B-lymphocyte mitogenicity of n-palmitoyl-cysteine and n-palmitoylglutamic Acid α-methyl esters", Biochemical and Biophysical Research Communications, Feb. 27, 1980, vol. 2, No. 4, pp. 1389-1396.
F. J. Zeelen, et al., "Synthesis of Stearoylamino-Acid", Recueil des Travaux Chemiques des Pays-Bas et de la Belgique, 1958, 77 , (3), XP-002743404, pp. 267-272.
Audrey Roth, et al., "Synthesis of Thiol-Reactive Lipopeptide Adjuvants. Incorporation into Liposomes and Study of Their Mitogenic Effect on Mouse Splenocytes", Bioconjugate Chem., 2004, 15, pp. 541-553.
Youssef Aachoui et al., "Synthetic adjuvants for vaccine formulation: Evaluation of new phytol derivatives in induction and persistence of specific immune response", Cellular Immunology, 271, 2011, pp. 308-318.
Motoyasu Onishi et al., "Hydroxypropyl-β-Cyclodextrin Spikes Local Inflammation That Induces Th2 Cell and T Follicular Helper Cell Responses to the Coadministered Antigen", J. Immunol., 2015, 194, pp. 2673-2682.

\* cited by examiner

US 10,100,008 B2

IMMUNOSTIMULATING AGENT

CROSS REFERENCES TO RELATED APPLICATIONS

This application is a continuation of International Patent Application No. PCT/JP2015/063155, filed on Apr. 24, 2015, and claims priority to Japanese Patent Application No. 2014-091142, filed on Apr. 25, 2014, and Japanese Patent Application No. 2015-039593, filed on Feb. 27, 2015, all of which are incorporated herein by reference in their entireties.

BACKGROUND OF THE INVENTION

Field of the Invention

The present invention relates to compounds which have a superior immunostimulatory effect and are useful as an immunostimulating agent, particularly an adjuvant. The present invention also relates to compositions containing such a compound, and vaccines containing such a compound and an antigen.

Discussion of the Background

Vaccines includes live vaccines wherein a pathogen is attenuated, whole particle vaccines wherein a pathogen is inactivated, and split vaccines wherein a pathogen is decomposed and only a particular component is extracted and purified. Of these, split vaccines require the addition of a compound or composition called adjuvant to enhance immunostimulatory ability thereof. Also, it is said that mucosal vaccines, cancer vaccines, and vaccines for a certain kind of allergy that are being increasingly researched and developed in recent years also require the addition of an adjuvant for the expression of the effects thereof. Examples of the adjuvants approved inside Japan at present include aluminum salts (aluminum hydroxide gel etc.) as precipitated adjuvant, squalane as oil adjuvant, MPL that is a variant of lipopolysaccharide LPS which is a constituent component of gram negative bacteria cell wall outer membrane intrinsically having immunogenicity. The research and development of adjuvants at the global level are also advancing taking note of nucleic acid derived from CpG and Poly I:C and the like, variants of bacteria constituent components that activate Toll-like receptor (TLR), variants of cytokines that stimulate immune system and the like. However, these existing adjuvants including those already approved inside Japan and those under research and development have the following problems.

As for aluminum salt which is a precipitated adjuvant, the adjuvant effect is questioned in some vaccines such as influenza HA vaccine, foot-and-mouth disease vaccine and the like. Also from the safety aspect, aluminum salt is known to often show granulation in the inoculation site, cause hyperimmunoglobulinemia E and the like. As for oil adjuvants such as squalene and the like, inoculation may be sometimes painful since viscosity increases by emulsifying, and inoculation site sometimes indurates since it has property to resist dispersion in the body and stay at the inoculation site. On the other hand, since MPL is a variant of LPS having immunogenicity, simultaneous inoculation with vaccine sometimes initiates strong inflammatory reaction, and sometimes accompanies pain and fever. Furthermore, adjuvants under development are also held to have safety problems such as allergy induction, strong inflammation reaction, fever initiation and the like. As for nucleic acid adjuvant, new problems are surfacing such as problems in synthesizing as a pharmaceutical product, for example, difficulty in chemical synthesis up to a chain length considered to afford an effective adjuvant effect and the like. Although adjuvants are requested to simultaneously show effectiveness and safety, conventional adjuvants already approved inside Japan and those under research and development fail to completely satisfy such request as the situation stands.

In the meantime, National Institute of Allergy and Infectious Diseases (NIAID) indicates the following 12 points regarding the safety of vaccine adjuvant. 1) free of induction of autoimmune response, 2) free of antigen having crossreactivity with human antigen, 3) free of induction of allergic hypersensitive reaction, 4) should be synthesized chemically pure, 5) free of carcinogenicity, 6) free of induction of response other than the object immune response, 7) should be a substance to be quickly metabolized in the body, 8) should be safe irrespective of inoculation method, 9) should be free of teratogenicity and reproductive toxicity, 10) should have preservation stability for at least one year, 11) should be selected for the object, 12) should tolerate side reaction developed at low frequency. Also, in the guideline of EMEA (European Medicine Agency) which is an organization responsible for examination of vaccine in Europe, 1) histological damage and granuloma formation of inoculation spot, 2) hypersensitivity and anaphylaxis, 3) pyrogenicity, 4) systemic toxicity, 5) reproduction toxicity, 6) genotoxicity (synthetic adjuvant alone) are recited as nonclinical toxicity test of adjuvant alone. While some parts are common or not common between US and Europe, at least the vaccine adjuvants to be developed from now should satisfy these requests.

As a compound having an immunomodulatory effect, for example, the compounds described in JP-A-4-230359; JP-A-59-219262; JP-A-63-264444; JP-A-62-63600; JP-A-5-507705; JP-A-11-302250; JP-A-5-186419; Cybulla, J. et al., Biochemical and Biophysical Research Communications 1980, 92(4), 1389-96; Zeelen, F. J. et al., Recueil des Travaux Chemiques des Pays-Bas et de la Belgique 1958, 77(3), 267-72; Roth, A. et al., Bioconjugate Chem., 2004, 15, 541-553; and Y. Aachoui et al., Cellular Immunology 271 (2011) 308-318, all of which are incorporated herein by reference in their entireties, have heretofore been reported. While Example 25 of JP-A-4-230359 discloses a compound wherein the group corresponding to $R^3$ and $R^4$ in the following formula (I) is an undecyl group ($C_{11}$ alkyl group), the compound is different from a compound represented by the formula (I) and its adjuvant activity is not sufficient. While Example 3 of JP-A-59-219262 discloses a compound wherein the group corresponding to $R^3$ and $R^4$ in the formula (I) is an unsaturated hydrocarbon group ($C_{17}$ alkenyl group), the compound is also different from a compound represented by the formula (I) and its adjuvant activity is not sufficient. While Tables 1 and 2 of JP-A-63-264444 disclose a compound wherein the group corresponding to $R^3$ and $R^4$ in the formula (I) is a long chain alkyl group ($C_{35}$ alkyl group) substituted by a keto group or a hydroxyl group, the compound is also different from a compound represented by the formula (I), and dispersibility of the compound in saline and the like has not been studied at all, and there is no report on the improvement of dispersibility to enhance the effect thereof by combining the compound with α-cyclodextrin.

JP-A-5-186419 discloses N,N'-bis(hexadecanoyl)-L-cystine di-tert-butyl ester (compound wherein the group corresponding to $R^3$ and $R^4$ in the formula (I) is a $C_{15}$ alkyl group) as a synthetic intermediate for a compound usable for vaccine adjuvant; however, its immunomodulatory effect is not reported at all, and there is no report suggesting use thereof as an immunostimulating agent or adjuvant. While both N,N'-bis(hexadecanoyl)-L-cystine dimethyl ester (compound wherein the group corresponding to R³ and R⁴ in the formula (I) is a C₁₅ alkyl group, CAS registry number: 73793-92-7, described in Cybulla, J. et al., Biochemical and Biophysical Research Communications 1980, 92(4), 1389-96) and N,N'-bis(octadecanoyl)-L-cystine dimethyl ester (compound wherein the group corresponding to R³ and R⁴ in the formula (I) is a C₁₇ alkyl group, CAS registry numbers: 121074-91-7 and 896442-54-9, described in Zeelen, F. J. et al., Recueil des Travaux Chemiques des Pays-Bas et de la Belgique 1958, 77(3), 267-72) are known compounds; however, their immunomodulatory effects are not reported at all, and there is no report suggesting use thereof as an immunostimulating agent or adjuvant.

On the other hand, Y. Aachoui et al., Cellular Immunology 271 (2011) 308-318 reports the results evaluating the adjuvant activity of phytol and a derivative thereof. This document describes that β-cyclodextrin was used for dissolving phytol in cell proliferation inhibitory assay; however, β-cyclodextrin was not used for the evaluation of antigen-specific antibody production. In addition, α-cyclodextrin is not described or suggested in Y. Aachoui et al., Cellular Immunology 271 (2011) 308-318.

Thus, there remains a need for compounds which have a superior immunostimulatory effect and are useful as an immunostimulating agent, particularly an adjuvant. There also remains a need for compositions containing such a compound, and vaccines containing such a compound and an antigen.

SUMMARY OF THE INVENTION

Accordingly, it is one object of the present invention to provide novel compounds which have a superior immunostimulatory effect and are useful as an immunostimulating agent, particularly an adjuvant.

It is another object of the present invention to provide novel compositions which contain such a compound.

It is another object of the present invention to provide novel vaccines containing such a compound and an antigen.

These and other objects, which will become apparent during the following detailed description, have been achieved by the inventors' discovery that compounds represented by the following formula (I) (hereinafter sometimes to be referred to as the compound of the present invention or compound (I)) have a superior immunostimulatory effect that it can enhance antigen-specific IgG1 subclass antibody production without inducing the production of IgE antibody.

In addition, the present inventors have conducted further studies of compound (I), and found that the solubility and dispersibility in saline tends to decrease as the chain length of the acyl group increases. The present inventors have conducted intensive studies in an attempt to improve the decreased dispersibility, and found that the dispersibility can be remarkably improved and, surprisingly, even its antigen-specific IgG1 subclass antibody production-enhancing effect (immunostimulatory effect) can be improved, by the addition of α-cyclodextrin.

Accordingly, the present invention provides the following:

(1) An immunostimulating agent comprising at least one kind of compound represented by the formula (I):

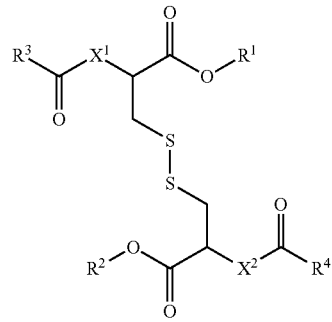

wherein

R¹ and R² are the same or different and each is a C₁₋₆ alkyl group;

R³ and R⁴ are the same or different and each is a C₁₂₋₃₇ alkyl group;

X¹ is —O—, —NR⁵— wherein R⁵ is a hydrogen atom or a C₁₋₆ alkyl group or —S—; and X² is —O—, —NR⁶— wherein R⁶ is a hydrogen atom or a C₁₋₆ alkyl group or —S—.

(2) The immunostimulating agent of (1), wherein R¹ and R² are each methyl.

(3) The immunostimulating agent of (1) or (2), wherein X¹ and X² are each —NH—.

(4) The immunostimulating agent of any one of (1) to (3), wherein R³ and R⁴ are the same or different and each is a C₁₂₋₃₅ alkyl group.

(5) The immunostimulating agent of any one of (1) to (4), wherein R³ and R⁴ are the same or different and each is a C₁₂₋₃₀ alkyl group.

(6) The immunostimulating agent of any one of (1) to (3), wherein the compound represented by the formula (I) is selected from the group consisting of N,N'-bis(hexadecanoyl)-L-cystine dimethyl ester,
N,N'-bis(2-heptylundecanoyl)-L-cystine dimethyl ester,
N,N'-bis[5,7,7-trimethyl-2-(1,3,3-trimethylbutyl)octanoyl]-L-cystine dimethyl ester,
N,N'-bis(tridecanoyl)-L-cystine dimethyl ester,
N,N'-bis(octadecanoyl)-L-cystine dimethyl ester,
N,N'-bis(triacontanoyl)-L-cystine dimethyl ester,
N,N'-bis(2-tetradecylhexadecanoyl)-L-cystine dimethyl ester,
N,N'-bis(2-octadecyleicosanoyl)-L-cystine dimethyl ester, and
N,N'-bis(docosanoyl)-L-cystine dimethyl ester.

(7) The immunostimulating agent of any one of (1) to (6), wherein the compound represented by the formula (I) is selected from the group consisting of N,N'-bis(hexadecanoyl)-L-cystine dimethyl ester,
N,N'-bis(2-heptylundecanoyl)-L-cystine dimethyl ester,
N,N'-bis[5,7,7-trimethyl-2-(1,3,3-trimethylbutyl)octanoyl]-L-cystine dimethyl ester,
N,N'-bis(tridecanoyl)-L-cystine dimethyl ester,
N,N'-bis(octadecanoyl)-L-cystine dimethyl ester, and
N,N'-bis(triacontanoyl)-L-cystine dimethyl ester.

(8) The immunostimulating agent of any one of (1) to (7), further comprising α-cyclodextrin.

(9) The immunostimulating agent of any one of (1) to (3), further comprising α-cyclodextrin, wherein $R^2$ and $R^4$ are the same or different and each is a $C_{29-37}$ alkyl group.

(10) The immunostimulating agent of any one of (1) to (9), wherein the agent is an adjuvant.

(11) A vaccine comprising the agent of any one of (1) to (10) and an antigen.

(12) A pharmaceutical composition comprising at least one kind of compound represented by the formula (I):

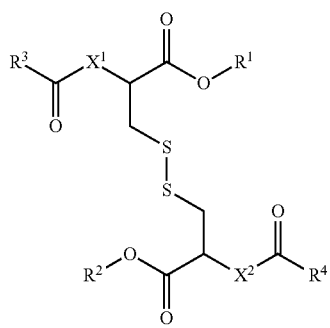

(I)

wherein $R^1$ and $R^2$ are the same or different and each is a $C_{1-6}$ alkyl group;

$R^2$ and $R^4$ are the same or different and each is a $C_{12-37}$ alkyl group;

$X^1$ is —O—, —NR$^5$— wherein $R^5$ is a hydrogen atom or a $C_{1-6}$ alkyl group or —S—; and $X^2$ is —O—, —NR$^6$— wherein $R^6$ is a hydrogen atom or a $C_{1-6}$ alkyl group or —S—, and α-cyclodextrin.

(13) The pharmaceutical composition of (12), wherein $R^1$ and $R^2$ are each methyl.

(14) The pharmaceutical composition of (12) or (13), wherein $X^1$ and $X^2$ are each —NH—.

(15) The pharmaceutical composition of any one of (12) to (14), wherein $R^3$ and $R^4$ are the same or different and each is a $C_{29-37}$ alkyl group.

(16) The pharmaceutical composition of any one of (12) to (14), wherein the compound represented by the formula (I) is selected from the group consisting of N,N'-bis(hexadecanoyl)-L-cystine dimethyl ester, N,N'-bis(2-heptylundecanoyl)-L-cystine dimethyl ester, N,N'-bis[5,7,7-trimethyl-2-(1,3,3-trimethylbutyl)octanoyl]-L-cystine dimethyl ester, N,N'-bis(tridecanoyl)-L-cystine dimethyl ester, N,N'-bis(octadecanoyl)-L-cystine dimethyl ester, N,N'-bis(triacontanoyl)-L-cystine dimethyl ester, N,N'-bis(2-tetradecylhexadecanoyl)-L-cystine dimethyl ester, N,N'-bis(2-octadecyleicosanoyl)-L-cystine dimethyl ester, and N,N'-bis(docosanoyl)-L-cystine dimethyl ester.

(17) A compound represented by the formula (I):

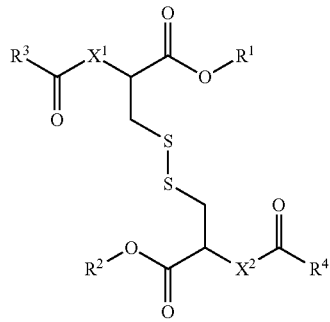

(I)

wherein $R^1$ and $R^2$ are the same or different and each is a $C_{1-6}$ alkyl group;

$R^3$ and $R^4$ are the same or different and each is a $C_{12-37}$ alkyl group;

$X^1$ is —O—, —NR$^5$— wherein $R^5$ is a hydrogen atom or a $C_{1-6}$ alkyl group or —S—; and $X^2$ is —O—, —NR$^6$— wherein $R^6$ is a hydrogen atom or a $C_{1-6}$ alkyl group or —S—

(excluding N,N'-bis(hexadecanoyl)-L-cystine dimethyl ester, N,N'-bis(hexadecanoyl)-L-cystine di-tert-butyl ester and N,N'-bis(octadecanoyl)-L-cystine dimethyl ester).

(18) The compound of (17), wherein $R^1$ and $R^2$ are each methyl.

(19) The compound of (17) or (18), wherein $X^1$ and $X^2$ are each —NH—.

(20) The compound of any one of (17) to (19), wherein $R^3$ and $R^4$ are the same or different and each is a $C_{12-35}$ alkyl group.

(21) The compound of any one of (17) to (20), wherein $R^3$ and $R^4$ are the same or different and each is a $C_{12-30}$ alkyl group.

(22) The compound of any one of (17) to (19), wherein $R^3$ and $R^4$ are the same or different and each is a $C_{29-37}$ alkyl group.

(23) A compound selected from the group consisting of N,N'-bis(2-heptylundecanoyl)-L-cystine dimethyl ester, N,N'-bis[5,7,7-trimethyl-2-(1,3,3-trimethylbutyl)octanoyl]-L-cystine dimethyl ester, N,N'-bis(tridecanoyl)-L-cystine dimethyl ester, N,N'-bis(triacontanoyl)-L-cystine dimethyl ester, N,N'-bis(2-tetradecylhexadecanoyl)-L-cystine dimethyl ester, N,N'-bis(2-octadecyleicosanoyl)-L-cystine dimethyl ester, and N,N'-bis(docosanoyl)-L-cystine dimethyl ester.

(24) A compound selected from the group consisting of N,N'-bis(2-heptylundecanoyl)-L-cystine dimethyl ester, N,N'-bis[5,7,7-trimethyl-2-(1,3,3-trimethylbutyl)octanoyl]-L-cystine dimethyl ester, N,N'-bis(tridecanoyl)-L-cystine dimethyl ester, and N,N'-bis(triacontanoyl)-L-cystine dimethyl ester.

(25) A vaccine comprising at least one kind of compound represented by the formula (I):

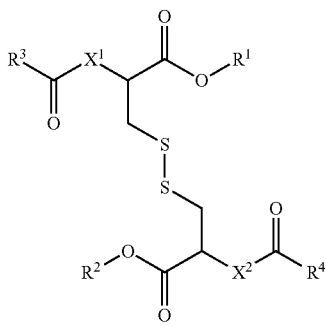

(I)

wherein
$R^1$ and $R^2$ are the same or different and each is a $C_{1-6}$ alkyl group;
$R^3$ and $R^4$ are the same or different and each is a $C_{12-37}$ alkyl group;
$X^1$ is —O—, —NR$^5$— wherein $R^5$ is a hydrogen atom or a $C_{1-6}$ alkyl group or —S—; and
$X^2$ is —O—, —NR$^6$— wherein $R^6$ is a hydrogen atom or a $C_{1-6}$ alkyl group or —S—, and
an antigen.

(26) The vaccine of (25), wherein $R^1$ and $R^2$ are each methyl.

(27) The vaccine of (25) or (26), wherein $X^1$ and $X^2$ are each —NH—.

(28) The vaccine of any one of (25) to (27), wherein $R^3$ and $R^4$ are the same or different and each is a $C_{12-35}$ alkyl group.

(29) The vaccine of any one of (25) to (28), wherein $R^3$ and $R^4$ are the same or different and each is a $C_{12-30}$ alkyl group.

(30) The vaccine of any one of (25) to (27), wherein the compound represented by the formula (I) is selected from the group consisting of
N,N'-bis(hexadecanoyl)-L-cystine dimethyl ester,
N,N'-bis(2-heptylundecanoyl)-L-cystine dimethyl ester,
N,N'-bis[5,7,7-trimethyl-2-(1,3,3-trimethylbutyl)octanoyl]-L-cystine dimethyl ester,
N,N'-bis(tridecanoyl)-L-cystine dimethyl ester,
N,N'-bis(octadecanoyl)-L-cystine dimethyl ester,
N,N'-bis(triacontanoyl)-L-cystine dimethyl ester,
N,N'-bis(2-tetradecylhexadecanoyl)-L-cystine dimethyl ester,
N,N'-bis(2-octadecyleicosanoyl)-L-cystine dimethyl ester, and
N,N'-bis(docosanoyl)-L-cystine dimethyl ester.

(31) The vaccine of any one of (25) to (29), wherein the compound represented by the formula (I) is selected from the group consisting of
N,N'-bis(hexadecanoyl)-L-cystine dimethyl ester,
N,N'-bis(2-heptylundecanoyl)-L-cystine dimethyl ester,
N,N'-bis[5,7,7-trimethyl-2-(1,3,3-trimethylbutyl)octanoyl]-L-cystine dimethyl ester,
N,N'-bis(tridecanoyl)-L-cystine dimethyl ester,
N,N'-bis(octadecanoyl)-L-cystine dimethyl ester, and
N,N'-bis(triacontanoyl)-L-cystine dimethyl ester.

(32) The vaccine of any one of (25) to (31), which is administered by a route selected from the group consisting of subcutaneous administration and intranasal administration.

EFFECT OF THE INVENTION

Since compound (I) has an antigen-specific IgG1 subclass antibody production-enhancing effect (immunostimulatory effect), it is useful as an immunostimulating agent. Particularly, since compound (I) has an immunostimulatory effect equivalent to or not less than that of conventional aluminum gel adjuvants, does not induce production of IgE antibody, and scarcely shows problematic allergy inducing activity of conventional aluminum gel adjuvants, it can be an effective and safe adjuvant.

According to the present invention, moreover, a pharmaceutical composition containing compound (I), which can be easily dissolved or dispersed in saline, can be provided. The pharmaceutical composition is superior in an antigen-specific IgG1 subclass antibody production-enhancing effect (immunostimulatory effect), and can be used as an immunostimulating agent.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
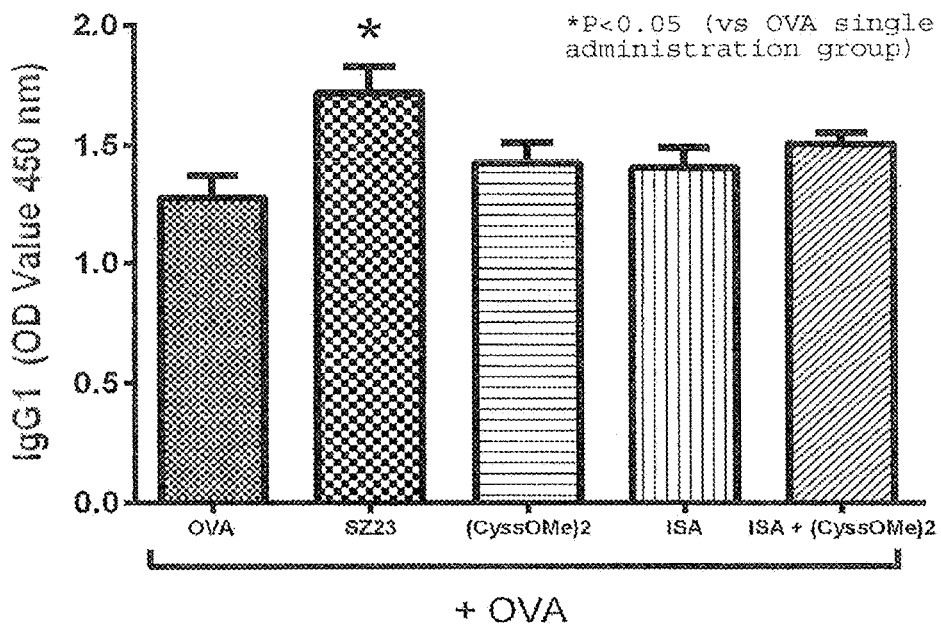
FIG. 1 is a graph showing the results of the evaluation test of adjuvant activity of N,N'-bis(2-heptylundecanoyl)-L-cystine dimethyl ester (SZ23: compound wherein the group corresponding to $R^3$ and $R^4$ in the formula (I) is $C_{17}$ alkyl group) in Example 1, wherein "OVA" shows OVA single administration group, "SZ23" shows SZ23 addition group, "(CyssOMe)$_2$" shows cystine dimethyl ester addition group, "ISA" shows isostearic acid addition group, and "ISA+(CyssOMe)$_2$" shows cystine dimethyl ester-isostearic acid mixture addition group.

The immunostimulating agent of the present invention contains at least one kind of compound represented by the following formula (I):

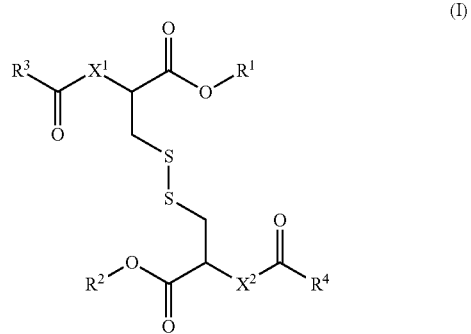

(I)

wherein
$R^1$ and $R^2$ are the same or different and each is a $C_{1-6}$ alkyl group;
$R^3$ and $R^4$ are the same or different and each is a $C_{12-37}$ alkyl group;
$X^1$ is —O—, —NR$^5$— wherein $R^5$ is a hydrogen atom or a $C_{1-6}$ alkyl group or —S—; and
$X^2$ is —O—, —NR$^6$— wherein $R^6$ is a hydrogen atom or a $C_{1-6}$ alkyl group or —S—.

Each group of the formula (I) is explained below.

$R^1$ and $R^2$ in the formula (I) are the same or different and each is a $C_{1-6}$ alkyl group.

The term "$C_{1-6}$ alkyl group" for $R^1$ or $R^2$ means a straight chain or branched chain alkyl group having 1 to 6 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, and the like. Among these, a $C_{1-3}$ alkyl group is preferable, and methyl is particularly preferable, from the aspect of easy availability and low cost.

While $R^1$ and $R^2$ may be the same or different, they are preferably the same.

In a preferable embodiment, $R^1$ and $R^2$ are the same or different and each is a $C_{1-3}$ alkyl group (e.g., methyl etc.).

$R^3$ and $R^4$ in the formula (I) are the same or different and each is a $C_{12-37}$ alkyl group.

The term "$C_{12-37}$ alkyl group" for $R^3$ or $R^4$ means a straight chain or branched chain alkyl group having 12 to 37 carbon atoms, and examples thereof include dodecyl, tridecyl, tetradecyl, pentadecyl, hexadecyl, heptadecyl, 2-heptyldecyl, 4,6,6-trimethyl-1-(1,3,3-trimethylbutyl)heptyl, octadecyl, nonadecyl, icosyl, eicosyl, henicosyl, heneicosyl, docosyl, tricosyl, tetracosyl, pentacosyl, hexacosyl, heptacosyl, octacosyl, nonacosyl, 2-tetradecylpentadecyl, triacontyl, hentriacontyl, dotriacontyl, tritriacontyl, tetratriacontyl, pentatriacontyl, hexatriacontyl, heptatriacontyl, 2-octadecylnonadecyl, and the like.

In one embodiment, $R^3$ and $R^4$ are the same or different and each may be a $C_{12-35}$ alkyl group. Particularly, a $C_{12-32}$ alkyl group is preferable, and a $C_{12-30}$ alkyl group is more preferable. Concretely, a $C_{12}$ alkyl group, $C_{13}$ alkyl group, $C_{14}$ alkyl group, $C_{15}$ alkyl group, $C_{16}$ alkyl group, $C_{17}$ alkyl group, $C_{18}$ alkyl group, $C_{19}$ alkyl group, $C_{20}$ alkyl group, $C_{21}$ alkyl group, $C_{22}$ alkyl group, $C_{23}$ alkyl group, $C_{24}$ alkyl group, $C_{25}$ alkyl group, $C_{26}$ alkyl group, $C_{27}$ alkyl group, $C_{28}$ alkyl group, $C_{29}$ alkyl group or $C_{39}$ alkyl group is more preferable. Since it is particularly superior in an IgG1 subclass antibody production-enhancing effect, a $C_{12-21}$ alkyl group or a $C_{28-30}$ alkyl group is particularly preferable. For example, a $C_{12}$ alkyl group, $C_{15}$ alkyl group, $C_{17}$ alkyl group, $C_{21}$ alkyl group or $C_{29}$ alkyl group is particularly preferable.

When the agent of the present invention further contains α-cyclodextrin in addition to compound (I), as mentioned below, $R^3$ and $R^4$ are the same or different and each may be a $C_{12-37}$ alkyl group (for example, $C_{12}$ alkyl group, $C_{13}$ alkyl group, $C_{14}$ alkyl group, $C_{15}$ alkyl group, $C_{16}$ alkyl group, $C_{17}$ alkyl group, $C_{18}$ alkyl group, $C_{19}$ alkyl group, $C_{20}$ alkyl group, $C_{21}$ alkyl group, $C_{22}$ alkyl group, $C_{23}$ alkyl group, $C_{24}$ alkyl group, $C_{25}$ alkyl group, $C_{26}$ alkyl group, $C_{27}$ alkyl group, $C_{28}$ alkyl group, $C_{29}$ alkyl group, $C_{30}$ alkyl group, $C_{31}$ alkyl group, $C_{32}$ alkyl group, $C_{33}$ alkyl group, $C_{34}$ alkyl group, $C_{35}$ alkyl group, $C_{36}$ alkyl group or $C_{37}$ alkyl group), and a $C_{29-37}$ alkyl group is more effective and preferable. Concretely, a $C_{29}$ alkyl group, $C_{30}$ alkyl group, $C_{31}$ alkyl group, $C_{32}$ alkyl group, $C_{33}$ alkyl group, $C_{34}$ alkyl group, $C_{35}$ alkyl group, $C_{35}$ alkyl group or $C_{37}$ alkyl group is more effective and preferable.

While $R^3$ and $R^4$ may be the same or different, they are preferably the same.

In one preferable embodiment of $R^3$ and $R^4$, they are the same or different and each is a $C_{12-36}$ alkyl group.

In another preferable embodiment of $R^3$ and $R^4$, they are the same or different and each is a $C_{12-32}$ alkyl group (more preferably a $C_{12-30}$ alkyl group, particularly preferably a $C_{12-21}$ alkyl group or a $C_{28-30}$ alkyl group). Concretely, a $C_{12}$ alkyl group, $C_{13}$ alkyl group, $C_{14}$ alkyl group, $C_{15}$ alkyl group, $C_{16}$ alkyl group, $C_{17}$ alkyl group, $C_{18}$ alkyl group, $C_{19}$ alkyl group, $C_{20}$ alkyl group, $C_{21}$ alkyl group, $C_{22}$ alkyl group, $C_{23}$ alkyl group, $C_{24}$ alkyl group, $C_{25}$ alkyl group, $C_{26}$ alkyl group, $C_{27}$ alkyl group, $C_{28}$ alkyl group, $C_{29}$ alkyl group or $C_{30}$ alkyl group is more preferable.

When the agent of the present invention further contains α-cyclodextrin in addition to compound (I), in one preferable embodiment of $R^3$ and $R^4$, they are each a $C_{29-37}$ alkyl group.

$X^1$ in the formula (I) is —O—, —NR$^5$— wherein $R^5$ is a hydrogen atom or a $C_{1-6}$ alkyl group or —S—.

The term "$C_{1-6}$ alkyl group" for $R^5$ is as defined for the "$C_{1-6}$ alkyl group" for the aforementioned $R^1$ or $R^2$, and specific examples and preferable embodiments thereof are also the same.

A preferable embodiment of $X^1$ is —NR$^5$— wherein $R^5$ is a hydrogen atom or a $C_{1-6}$ alkyl group.

A more preferable embodiment of $X^1$ is —NH—.

$X^2$ in the formula (I) is —O—, —NR$^6$— wherein $R^6$ is a hydrogen atom or a $C_{1-6}$ alkyl group or —S—.

The term "$C_{1-6}$ alkyl group" for $R^6$ is as defined for the "$C_{1-6}$ alkyl group" for the aforementioned $R^1$ and $R^2$, and specific examples and preferable embodiments thereof are also the same.

In a preferable embodiment, $X^2$ is —$NR^6$— wherein $R^6$ is a hydrogen atom or a $C_{1-6}$ alkyl group.

In a more preferable embodiment, $X^2$ is —NH—.

One embodiment of preferable compound (I) is compound (I) wherein $R^1$ and $R^2$ are the same or different and each is a $C_{1-3}$ alkyl group (e.g., methyl etc.), $R^3$ and $R^4$ are the same or different and each is a $C_{12-37}$ alkyl group (more preferably $C_{12-35}$ alkyl group), $X^1$ is —$NR^5$— wherein $R^5$ is a hydrogen atom or a $C_{1-6}$ alkyl group, and $X^2$ is —$NR^6$— wherein $R^6$ is a hydrogen atom or a $C_{1-6}$ alkyl group, more preferably, compound (I) wherein $R^1$ and $R^2$ are each methyl, $R^3$ and $R^4$ are the same or different and each is a $C_{12-37}$ alkyl group (more preferably $C_{12-35}$ alkyl group), and $X^1$ and $X^2$ are each —NH—.

Other embodiment of preferable compound (I) is compound (I) wherein $R^1$ and $R^2$ are the same or different and each is a $C_{1-3}$ alkyl group (e.g., methyl etc.), $R^3$ and $R^4$ are the same or different and each is a $C_{12-32}$ alkyl group (more preferably $C_{12-30}$ alkyl group, particularly preferably $C_{12-21}$ alkyl group or $C_{28-30}$ alkyl group), $X^1$ is —$NR^5$— wherein $R^5$ is a hydrogen atom or a $C_{1-6}$ alkyl group, and $X^2$ is —$NR^6$— wherein $R^6$ is a hydrogen atom or a $C_{1-6}$ alkyl group.

More preferable compound (I) is compound (I) wherein $R^1$ and $R^2$ are each methyl, $R^3$ and $R^4$ are the same or different and each is a $C_{12-32}$ alkyl group (more preferably $C_{12-30}$ alkyl group, particularly preferably $C_{12-21}$ alkyl group or $C_{28-30}$ alkyl group), and $X^1$ and $X^2$ are each —NH—.

Specific examples of preferable compound (I) include
N,N'-bis(hexadecanoyl)-L-cystine dimethyl ester,
N,N'-bis(2-heptylundecanoyl)-L-cystine dimethyl ester,
N,N'-bis[5,7,7-trimethyl-2-(1,3,3-trimethylbutyl)octanoyl]-L-cystine dimethyl ester,
N,N'-bis(tridecanoyl)-L-cystine dimethyl ester,
N,N'-bis(octadecanoyl)-L-cystine dimethyl ester,
N,N'-bis(triacontanoyl)-L-cystine dimethyl ester,
N,N'-bis(2-tetradecylhexadecanoyl)-L-cystine dimethyl ester,
N,N'-bis(2-octadecyleicosanoyl)-L-cystine dimethyl ester,
N,N'-bis(docosanoyl)-L-cystine dimethyl ester, and the like.

Compound (I) is more preferably N,N'-bis(2-heptylundecanoyl)-L-cystine dimethyl ester, N,N'-bis[5,7,7-trimethyl-2-(1,3,3-trimethylbutyl)octanoyl]-L-cystine dimethyl ester, N,N'-bis(tridecanoyl)-L-cystine dimethyl ester, N,N'-bis(triacontanoyl)-L-cystine dimethyl ester, N,N'-bis(2-tetradecylhexadecanoyl)-L-cystine dimethyl ester, N,N'-bis(2-octadecyleicosanoyl)-L-cystine dimethyl ester or bis(docosanoyl)-L-cystine dimethyl ester, and particularly preferably N,N'-bis(2-heptylundecanoyl)-L-cystine dimethyl ester, N,N'-bis[5,7,7-trimethyl-2-(1,3,3-trimethylbutyl)octanoyl]-L-cystine dimethyl ester, N,N'-bis(tridecanoyl)-L-cystine dimethyl ester, N,N'-bis(triacontanoyl)-L-cystine dimethyl ester or bis(docosanoyl)-L-cystine dimethyl ester.

Compound (I) other than N,N'-bis(hexadecanoyl)-L-cystine dimethyl ester, N,N'-bis(hexadecanoyl)-L-cystine di-tert-butyl ester and N,N'-bis(octadecanoyl)-L-cystine dimethyl ester (e.g., N,N'-bis(2-heptylundecanoyl)-L-cystine dimethyl ester, N,N'-bis[5,7,7-trimethyl-2-(1,3,3-trimethylbutyl)octanoyl]-L-cystine dimethyl ester, N,N'-bis(tridecanoyl)-L-cystine dimethyl ester, N,N'-bis(triacontanoyl)-L-cystine dimethyl ester, N,N'-bis(2-tetradecylhexadecanoyl)-L-cystine dimethyl ester, N,N'-bis(2-octadecyleicosanoyl)-L-cystine dimethyl ester, and N,N'-bis(docosanoyl)-L-cystine dimethyl ester etc.) is a novel compound.

Synthesis of Compound (I)

A production method of compound (I) is explained below.

While a representative production method is described below as an example of the production method of compound (I), the production method is not limited thereto.

Among compounds (I), compound (Ia) wherein $R^3$ and $R^4$ are the same can be produced by, for example, the following reaction scheme A or a method analogous thereto.

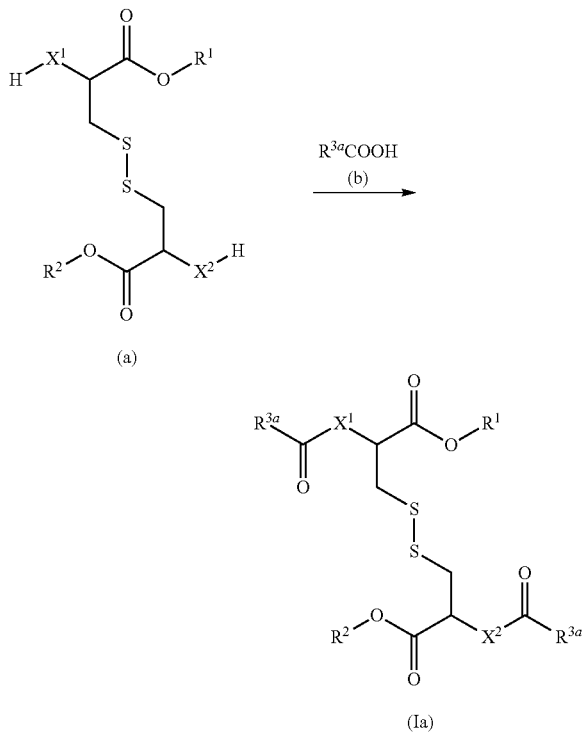

Reaction scheme A wherein $R^{3a}$ is as defined for $R^3$ or $R^4$, and other symbols are as defined above.

Compound (Ia) can be produced by reacting compound (a) with compound (b) in the presence of a condensing agent.

The amount of compound (b) to be used is generally 1.5 to 10 equivalents, preferably 2 to 4 equivalents, relative to 1 equivalent of compound (a).

Examples of the condensing agent include carbodiimides such as 1,3-dicyclohexylcarbodiimide, 1-cyclohexyl-3-morpholinoethylcarbodiimide, 1-cyclohexyl-3-(4-diethylaminocyclohexyl)carbodiimide, 1,3-diethylcarbodiimide, 1,3-diisopropylcarbodiimide, 1-ethyl-3-(3-dimethylaminopropyl)carbodiimide and the like or a salt thereof and the like.

The amount of the condensing agent to be used is generally 1.5 to 10 equivalents, preferably 2 to 4 equivalents, relative to 1 equivalent of compound (a).

This reaction may be performed in the presence of a base when desired.

Examples of the base include alkali metal hydroxides (e.g., lithium hydroxide, sodium hydroxide, potassium hydroxide etc.), alkaline earth metal hydroxides (e.g., magnesium hydroxide, calcium hydroxide etc.), alkali metal carbonates (e.g., sodium carbonate, potassium carbonate etc.), alkali metal hydrogen carbonates (e.g., sodium hydrogen carbonate, potassium hydrogen carbonate etc.), organic bases (e.g., trimethylamine, triethylamine, diisopropylethylamine, pyridine, 4-dimethylaminopyridine, picoline, N-methylpyrrolidine, N-methylmorpholine, N,N-dimethylaniline, 1,5-diazabicyclo[4.3.0]-5-nonene, 1,4-diazabicyclo[2.2.2]octane, 1,8-diazabicyclo[5.4.0]-7-undecene, tetramethylguanidine etc.), organic lithiums (e.g., methyllithium, n-butyllithium, sec-butyllithium, tert-butyllithium etc.), lithium amides (e.g., lithiumdiisopropylamide etc.) and the like.

The amount of the base to be used is generally 1.5 to 10 equivalents, preferably 2 to 6 equivalents, relative to 1 equivalent of compound (a).

Furthermore, this reaction may be performed in the presence of a condensation promoter when desired.

Examples of the condensation promoter include 1-hydroxybenzotriazole (HOBt), a hydrate thereof and the like.

The amount of the condensation promoter to be used is generally 0.01 to 10 equivalents, preferably 1 to 4 equivalents, relative to 1 equivalent of compound (a).

In this reaction, moreover, a mixed acid anhydride of compound (b) may be used instead of compound (b). The mixed acid anhydride can be obtained by, for example, first reacting compound (b) with alkyl chlorocarbonate (e.g., methyl chlorocarbonate, ethyl chlorocarbonate, isobutyl chlorocarbonate) and the like in the presence of a base.

This reaction is preferably performed in a solvent inert to the reaction. While such solvent is not particularly limited as long as the reaction proceeds, examples thereof include ethers (e.g., 1,4-dioxane, tetrahydrofuran, diethyl ether, tert-butyl methyl ether, diisopropyl ether, ethylene glycol dimethylether), esters (e.g., ethyl formate, ethyl acetate, butyl acetate), hydrocarbon halides (e.g., dichloromethane, chloroform, carbon tetrachloride, trichloroethylene), hydrocarbons (e.g., hexane, benzene, toluene), amides (e.g., N,N-dimethylformamide, N,N-dimethylacetamide), sulfoxides (e.g., dimethyl sulfoxide) and the like. Two or more kinds of these solvents may be mixed and used at an appropriate ratio.

The reaction temperature is generally −80 to 150° C., preferably 10 to 100° C.

The reaction time generally 0.5 to 48 hr, preferably 10 to 30 hr.

Of compounds (I), examples of the method of obtaining compound (Ib) wherein $R^3$ and $R^4$ are different:

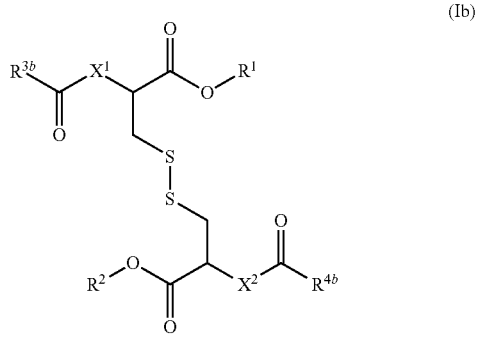

(Ib)

wherein $R^{3b}$ is as defined for $R^3$, $R^{4b}$ is as defined for $R^4$, and other symbols are as defined above,
include a method of reacting compound (a) with a mixture of $R^{3b}COOH$ and $R^{4b}COOH$ by a method similar to that of the above-mentioned reaction scheme A to give a mixture with a compound wherein $R^3$ and $R^4$ are the same, a method of obtaining the same by the following steps (1) to (3), and the like.

(1) a step of reacting a compound which is compound (a), wherein a protecting group is introduced into $X^2$, with $R^{3b}COOH$ by a method similar to that of the above-mentioned reaction scheme A;

(2) a step of deprotecting the obtained compound; and (3) a step of reacting the obtained compound with $R^{4b}COOH$ by a method similar to that of the above-mentioned reaction scheme A.

As a protecting group, those generally used in the peptide chemistry and the like may be used and, as a method for the introduction or removal of the protecting group, a method known per se may be used and, for example, the method described in Protective Groups in Organic Synthesis, John Wiley and Sons (1980), which is incorporated herein by reference in its entirety, and the like can be performed.

As compound (a), a commercially available product can be easily obtained, or can be produced according to a method known per se or a method analogous thereto. For example, compound (a) wherein $X^1$ or $X^2$ is —NH— can be produced by reacting cysteine alkyl ester in the presence of an oxidant and the like so that these thiol groups will form a disulfide bond. The method known per se, for example, the method described in J. Org. Chem., 60 (11), pp. 3266-3267 (1995), which is incorporated herein by reference in its entirety, may be used. The cysteine dialkyl ester can be easily obtained as a commercially available product, for example, wherein alkyl is methyl, ethyl, n-propyl, isopropyl, n-butyl, isobutyl, sec-butyl, tert-butyl, n-pentyl, iso-pentyl, n-hexyl, iso-hexyl and the like. For example, compound (a) wherein $X^1$ or $X^2$ is —O— can be produced by using 3-mercaptolactic acid alkyl ester in place of the cysteine alkyl ester in the above-mentioned method. The 3-mercaptolactic acid alkyl ester can be easily obtained as a commercially available product, for example, wherein alkyl is methyl, ethyl and the like.

Examples of other methods for obtaining compound (Ib) wherein $R^3$ and $R^4$ are different include 1) a method including reacting two kinds of acyl cysteines having different acyl groups in the presence of an oxidant and the like so that these thiol groups will form a disulfide bond, 2) a method including reacting a compound wherein a functional group (e.g., pyridinesulphenyl group etc.) capable of forming a disulfide bond with a thiol group is introduced into a thiol group of acyl cysteine with acyl cysteine having a different acyl group, 3) a method including introducing different acyl groups into two amino groups of cysteine by using different acylating agents and the like, and the like.

The method of the aforementioned 1) can be performed, for example, according to the method described in WO 2009/143299, which is incorporated herein by reference in its entirety, and the like. Of the methods of the aforementioned 2), the step of introducing a functional group (e.g., pyridinesulphenyl group etc.) capable of forming a disulfide bond with a thiol group into the thiol group of acyl cysteine can be performed, for example, according to the method described in ACS Chemical Biology, 8(6), pp. 1283-1290 (2013), which is incorporated herein by reference in its entirety, and the step of reacting the compound obtained by the step with acyl cysteine can be performed, for example, according to the method described in WO 2010/147831, which is incorporated herein by reference in its entirety, and the like. The method of the aforementioned 3) can be performed, for example, according to the method described in Heterocycles, 52(1), pp. 425-442 (2000), which is incorporated herein by reference in its entirety, and the like.

Compound (I) produced by a method such as the above can be isolated and purified by, for example, general separation means such as column chromatography, recrystallization, solvent washing and the like.

When compound (I) contains an optical isomer, a stereoisomer, a positional isomer or a rotamer, these are also included as compound (I), and each can be obtained as a single product by a synthesis method and a separation method known per se (concentration, solvent extraction, column chromatography, recrystallization, solvent washing etc.). For example, when an optical isomer is present in compound (I), an optical isomer resolved from the compound is also encompassed in compound (I).

An optical isomer can be produced by a method known per se. Specifically, an optical isomer is obtained by using an optically active synthetic intermediate, or optical resolution of the final product racemate according to a conventional method.

Compound (I) may be a crystal, and is encompassed in compound (I) whether the crystal form is single or a crystal mixture. A crystal can be produced by crystallization by applying a crystallization method known per se.

Compound (I) may be any of a hydrate, a non-hydrate, a solvate and a non-solvate.

Compound (I) labeled with an isotope (e.g., $^2H$, $^3H$, $^{13}C$, $^{14}C$, $^{15}N$, $^{35}S$) and the like is also encompassed in the compound of the present invention.

Since compound (I) has an antigen-specific IgG1 subclass antibody production-enhancing effect (immunostimulatory effect), it is useful as an immunostimulating agent. The immunostimulating agent of the present invention (hereinafter sometimes to be simply abbreviated as "the agent of the present invention") may be compound (I) per se, or may be obtained by formulating compound (I) by using a pharmacologically acceptable carrier and the like.

As a pharmacologically acceptable carrier that the agent of the present invention may contain, various conventional organic or inorganic carrier substances are used as preparation materials, which are added as excipient, lubricant, binder or disintegrant in solid preparations; solvent, solubilizing agent, suspending agent, isotonicity agent, buffering agent or soothing agent in liquid preparations, and the like. Where necessary, preparation additives such as preservative, antioxidant, colorant, sweetening agent and the like can also be used.

The agent of the present invention may further contain α-cyclodextrin in addition to compound (I). When the agent of the present invention further contains α-cyclodextrin, the dispersibility of compound (I) is improved, and surprisingly, even the antigen-specific IgG1 subclass antibody production-enhancing effect (immunostimulatory effect) can be further improved. In compounds (I), the number of carbon atoms of the alkyl group for $R^3$ or $R^4$ may be not less than 12 and not more than 37 (for example, $C_{12}$ alkyl group, $C_{13}$ alkyl group, $C_{14}$ alkyl group, $C_{15}$ alkyl group, $C_{16}$ alkyl group, $C_{17}$ alkyl group, $C_{18}$ alkyl group, $C_{19}$ alkyl group, $C_{20}$ alkyl group, $C_{21}$ alkyl group, $C_{22}$ alkyl group, $C_{23}$ alkyl group, $C_{24}$ alkyl group, $C_{25}$ alkyl group, $C_{26}$ alkyl group, $C_{27}$ alkyl group, $C_{28}$ alkyl group, $C_{29}$ alkyl group, $C_{30}$ alkyl group, $C_{31}$ alkyl group, $C_{32}$ alkyl group, $C_{33}$ alkyl group, $C_{34}$ alkyl group, $C_{35}$ alkyl group, $C_{36}$ alkyl group or $C_{37}$ alkyl group). Particularly, when the dispersibility of compound (I) wherein the number of carbon atoms of the alkyl group for $R^3$ or $R^4$ is not less than 29 and that of compound (I) wherein the number of carbon atoms of the alkyl group for $R^3$ or $R^4$ is less than 29 are compared, the former tends to show weaker dispersibility in saline and the like than the latter. Therefore, it is more effective and preferable for the agent of the present invention containing compound (I), wherein $R^3$ and $R^4$ are the same or different and each is $C_{29-37}$ alkyl group, to further contain α-cyclodextrin in addition to compound (I). However, because of getting better results by addition of α-cyclodextrin, even if the agent of the present invention may further contain α-cyclodextrin in addition to compound (I), $R^3$ and $R^4$ are the same or different and each is a $C_{12-37}$ alkyl group, preferably a $C_{12-35}$ alkyl group. Particularly, a $C_{12-32}$ alkyl group is preferable, and a $C_{12-30}$ alkyl group is more preferable. Concretely, a $C_{12}$ alkyl group, $C_{13}$ alkyl group, $C_{14}$ alkyl group, $C_{15}$ alkyl group, $C_{16}$ alkyl group, $C_{17}$ alkyl group, $C_{18}$ alkyl group, $C_{19}$ alkyl group, $C_{20}$ alkyl group, $C_{21}$ alkyl group, $C_{22}$ alkyl group, $C_{23}$ alkyl group, $C_{24}$ alkyl group, $C_{25}$ alkyl group, $C_{26}$ alkyl group, $C_{27}$ alkyl group, $C_{28}$ alkyl group, $C_{29}$ alkyl group or $C_{30}$ alkyl group is more preferable. Since it is particularly superior in an IgG1 subclass antibody production-enhancing effect, a $C_{12-21}$ alkyl group or a $C_{28-30}$ alkyl group is particularly preferable. For example, a $C_{12}$ alkyl group, $C_{15}$ alkyl group, $C_{17}$ alkyl group, $C_{21}$ alkyl group or $C_{29}$ alkyl group is particularly preferable.

When the agent of the present invention further contains α-cyclodextrin in addition to compound (I), preferred as compound (I) is compound (I) wherein $R^1$ and $R^2$ are the same or different and each is a $C_{1-3}$ alkyl group (e.g., methyl etc.), $R^3$ and $R^4$ are the same or different and each is a $C_{12-37}$ alkyl group, $X^1$ is —$NR^5$— wherein $R^5$ is a hydrogen atom or a $C_{1-6}$ alkyl group, and $X^2$ is —$NR^6$— wherein $R^6$ is a hydrogen atom or a $C_{1-6}$ alkyl group, more preferred is compound (I) wherein $R^1$ and $R^2$ are each methyl, $R^3$ and $R^4$ are the same or different and each is a $C_{12-37}$ alkyl group, and $X^1$ and $X^2$ are each —NH—.

When the agent of the present invention further contains α-cyclodextrin in addition to compound (I) to achieve higher effectiveness, still more preferred as compound (I) is compound (I) wherein $R^1$ and $R^2$ are the same or different and each is a $C_{1-3}$ alkyl group (e.g., methyl etc.), $R^3$ and $R^4$ are the same or different and each is a $C_{29-37}$ alkyl group, $X^1$ is —$NR^5$— wherein $R^5$ is a hydrogen atom or a $C_{1-6}$ alkyl group, and $X^2$ is —$NR^6$— wherein $R^6$ is a hydrogen atom or a $C_{1-6}$ alkyl group, further preferred is compound (I) wherein $R^1$ and $R^2$ are each methyl, $R^3$ and $R^4$ are the same or different and each is a $C_{29-37}$ alkyl group, and $X^1$ and $X^2$ are each —NH—.

Specific examples of preferable compound (I) when the agent of the present invention further contains α-cyclodextrin in addition to compound (I) include N,N'-bis(hexadecanoyl)-L-cystine dimethyl ester,
N,N'-bis(2-heptylundecanoyl)-L-cystine dimethyl ester, N,N'-bis[5,7,7-trimethyl-2-(1,3,3-trimethylbutyl)octanoyl]-L-cystine dimethyl ester,
N,N'-bis(tridecanoyl)-L-cystine dimethyl ester,
N,N'-bis(octadecanoyl)-L-cystine dimethyl ester,
N,N'-bis(triacontanoyl)-L-cystine dimethyl ester,
N,N'-bis(2-tetradecylhexadecanoyl)-L-cystine dimethyl ester,
N,N'-bis(2-octadecyleicosanoyl)-L-cystine dimethyl ester,
N,N'-bis(docosanoyl)-L-cystine dimethyl ester, and the like, and further include, for higher effectiveness,
N,N'-bis(2-tetradecylhexadecanoyl)-L-cystine dimethyl ester,
N,N'-bis(2-octadecyleicosanoyl)-L-cystine dimethyl ester and the like.

In the present invention, the term α-cyclodextrin refers to cyclic oligosaccharide wherein six D-glucoses form a cyclic structure with α1→4 bond.

The α-cyclodextrin used in the present invention may be in the form of a derivative. While such derivative is not particularly limited as long as it has the skeleton of α-cyclodextrin, examples thereof include derivatives wherein α-cyclodextrin is chemically modified by methylation and the like or enzymatically modified by maltosylation and the like, and the like.

While α-cyclodextrin used in the present invention can be produced by, for example, enzymatically converting starch by cyclodextrin glucanotransferase, and the like, the production method is not limited thereto and it may be produced by a method known per se. In addition, a commercially available product may be used, and it is convenient and preferable.

While the weight ratio of compound (I) and α-cyclodextrin (compound (I):α-cyclodextrin) in the agent of the present invention is not particularly limited, it is preferably 1:0.0002 to 2.0000, more preferably 1:0.002 to 0.2.

Examples of the dosage form of the agent of the present invention include oral preparations such as tablet (including sugar-coated tablet, film-coated tablet, sublingual tablet, orally disintegrating tablet), capsule (including soft capsule, microcapsule), granule, powder, troche, syrup, emulsion, suspension and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, drip infusion, eye drop, pulmonary preparation (inhalant) and the like. These preparations may be controlled-release preparations (e.g., sustained-release microcapsule) such as immediate-release preparation, sustained-release preparation and the like.

When the agent of the present invention is an oral preparation, coating may be performed where necessary, aiming at masking taste, enteric property or sustainability. Examples of the coating base to be used for coating include various known coating bases.

The agent of the present invention can be produced by a method used conventionally in the technical field of preparation formulation, for example, the method described in the Japanese Pharmacopoeia, 16th Edition, which is incorporated herein by reference in its entirety, and the like.

The agent of the present invention can be processed into a preparation for children, in addition to that for adults.

The subject of administration of the agent of the present invention is not particularly limited as long as it is an animal having an immune system. Examples thereof include mammals (e.g., human, mouse, rat, rabbit, dog, cat, bovine, horse, swine, monkey etc.), birds (e.g., chicken, duck, goose etc.) and the like. The agent of the present invention can be safely administered orally or parenterally (e.g., topical, rectal, intravenous administration) to them.

While the mechanism of the antigen specific IgG1 subclass antibody production-enhancing effect (immunostimulatory effect) of compound (I) is not clear, it is considered, as shown in the below-mentioned Examples, that antigen-specific IgG1 antibody production is enhanced by acting on antigen presenting cells (e.g., monocytic cell, macrophage, dendritic cell etc.) to promote cell proliferation thereof. Accordingly, the agent of the present invention is useful as a growth promoter for antigen presenting cells.

Since compound (I) has a superior adjuvant activity as shown in the below-mentioned Examples, the agent of the present invention is useful as an adjuvant.

The term "adjuvant" in the present invention is a generic term for substances that increase antibody production and enhance immune response when combined with an antigen.

When the agent of the present invention is used as an adjuvant, the dosage form thereof may be, for example, an aqueous or a non-aqueous (e.g., oily etc.) solution, suspension, emulsion and the like. These can be prepared by mixing compound (I) with a pharmacologically acceptable carrier (e.g., solvent, suspending agent etc.) and performing a method such as manual shaking, mechanical shaking, ultrasonic dispersing, dispersing by a homomixer, self emulsification, membrane emulsification, D-phase emulsification method, vacuum emulsification method, ultra-high pressure emulsification method and the like.

The agent of the present invention may be used in combination with other adjuvant. Examples of other adjuvant include Freund's Incomplete Adjuvant, Freund's Complete Adjuvant, particulates (e.g., urate crystals, silica, aluminum hydroxide gel, polystyrene, asbestos, titanium dioxide, black nickel oxide etc.), lipopolysaccharide (LPS), monophosphoryl lipid A (MPLA), flagellin, cholera toxin B subunit (CTB), β-glucan, chitosan, saponin, squalene, α-GalCer, lipopeptide (e.g., Pam2CSK4, Pam3CSK4 etc.), liposome, nucleic acid (e.g., ssDNA, dsDNA, ssRNA, dsRNA, CpG, polyinosinic polycytidylic acid (Poly I:C) etc.), probiotic lactic acid bacterium (e.g., *lactobacillus plantarum, lactobacillus casei, lactobacillus lactis* etc.), cytokine (e.g., interleukin-1, interleukin-2, interleukin-7, interleukin-12, interleukin-15, interleukin-18, TNF-α, GM-CSF, IFN-α etc.) and the like.

The present invention also provides a vaccine containing the agent (or the compound) of the present invention and an antigen. The compound to be contained in the vaccine of the present invention may be one similar to compound (I) contained in the agent of the present invention. Examples of the compound that the vaccine of the present invention may contain include those recited as examples of the compound contained in the agent of the present invention.

The antigen to be used in the present invention is not particularly limited as long as it is a substance capable of inducing an immune reaction, and examples thereof include allergen, pathogen antigen, self antigen in the living body, tumor antigen and the like.

The allergen to be used in the present invention can be pollen allergen, food allergen, or house dust allergen. The pollen allergen is not particularly limited, and examples thereof include cedar pollen allergen, Japanese cypress pollen allergen, ragweed allergen, *Dactylis glomerata* allergen and the like. The food allergen is not particularly limited, and examples thereof include casein, lactalbumin, lactoglobulin, ovomucoid, ovalbumin, conalbumin and the like. The house dust allergen is not particularly limited, and examples thereof include mites allergen, cat allergen, and the like.

The pathogen antigen to be used in the present invention can be pathogenic virus antigen, pathogenic microorganism antigen or pathogenic protozoan antigen. The pathogenic virus antigen is not particularly limited, and examples thereof include antigen of virus such as human immunodeficiency virus (HIV), hepatitis virus (e.g., type A, type B, type C, type D and type E hepatitis virus etc.), influenza virus, simple herpes virus, West Nile fever virus, human papilloma virus, horse encephalitis virus, human T cell leukemia virus (e.g., HTLV-I etc.), polio virus, varicella-zoster virus, mumps virus, rotavirus, norovirus, RS virus, measles virus, ebola virus and the like, and the antigen of influenza virus is particularly preferably used. The pathogenic microorganism antigen is not particularly limited, and examples thereof include antigens expressed in pathogenic bacterium (e.g., *Haemophilus influenzae* type B (Hib), pneumococcus, *clostridium tetani, corynebacterium diphtheriae, bordetella pertussis*, cholera, *salmonella, bacillus typhosus*, chlamydiae, *mycobacteria, legionella* etc.), pathogenic yeast (e.g., *Aspergillus, Candida* etc.) and the like. The pathogenic protozoan antigen is not particularly limited, and examples thereof include antigens expressed in malaria, schistosome and the like.

The self antigen in the living body, which is to be used in the present invention, is not particularly limited, and examples thereof include amyloid β, prion in neurological diseases such as Alzheimer's disease, Creutzfeldt-Jakob disease and the like; ApoB100, angiotensin I, angiotensin II in circulatory diseases such as arteriosclerosis, hypertension and the like; insulin, IL-5 in autoimmune/allergic diseases such as Type I diabetes mellitus, bronchial asthma and the like; IL-6, TNF-α in rheumatoid arthritis, and the like.

The tumor antigen to be used in the present invention can be an antigen of a solid tumor such as epithelial and non-epithelial tumors or an antigen of a tumor in hematopoietic tissue. The solid tumor antigen is not particularly limited, and examples thereof include MART-1/Melan-A, Mage-1, Mage-3, gp100, tyrosinase, tyrosinase-related protein 2 (trp2), CEA, PSA, CA-125, erb-2, Muc-1, Muc-2, TAG-72, AES, ISP, C-lectin, NY-ESO-1, galectin-4/NY-CO-27, Pec60, HER-2/erbB-2/neu, telomerase, G250, Hsp105, point mutated ras oncogene, point mutated p53 oncogene, carcinoembryonic antigen and the like. The antigen of a tumor (e.g., leukemia) in hematopoietic tissue is not particularly limited, and examples thereof include proteinase 3, WT-1, hTERT, PRAME, PML/RAR-a, DEK/CAN, cyclophilin B, TEL-MAL1, BCR-ABL, OFA-iLRP, Survivin, idiotype, Sperm protein 17, SPAN-Xb, CT-27, MUC1 and the like.

The vaccine of the present invention may be administered by a route selected from the group consisting of oral, intramuscular, transdermal, interdermal, subcutaneous, intraperitoneal, intratracheal, intranasal(transnasal), intraocular, vaginal, rectal, intravenous, intraintestinal and inhalation administrations, particularly preferably subcutaneous or intranasal (transnasal) administration.

The content of the antigen in the vaccine of the present invention may be an effective amount that functions as a vaccine, and the amount can be determined by those of ordinary skill in the art based on, for example, tests using an experiment animal and the like, without requiring undue experiments. Specifically, the content of the antigen in the vaccine of the present invention is generally 1 to 100 μg, based on the total weight of the vaccine.

While the content of the immunostimulating agent of the present invention in the vaccine of the present invention is not particularly limited and may be appropriately adjusted according to, for example, the kind of antigen, subject of administration, administration form, administration route and the like, it is generally 2 μg to 20 mg, preferably 20 μg to 200 μg, based on the total weight of the vaccine, for oral, intramuscular, transdermal, interdermal, subcutaneous or intraperitoneal administration and generally 0.01 μg to 1 mg, preferably 0.1 μg to 100 μg, based on the total weight of the vaccine, for intratracheal, intranasal(transnasal), intraocular, vaginal, rectal, intravenous, intraintestinal or inhalation administration.

The vaccine of the present invention may contain a pharmacologically acceptable carrier in addition to the immunostimulating agent of the present invention and antigen. Examples of the pharmacologically acceptable carrier that the vaccine of the present invention may contain include those recited as examples of the pharmacologically acceptable carrier that the agent of the present invention may contain.

The vaccine of the present invention may further contain another adjuvant. Examples of other adjuvant include those recited as examples of the adjuvant that can be used in combination with the agent of the present invention.

Examples of the dosage form of the vaccine of the present invention include those recited as examples of the dosage form of the agent of the present invention.

The vaccine of the present invention can be produced by a method used conventionally in the technical field of preparation formulation, for example, the method described in the Japanese Pharmacopoeia, 16th Edition, which is incorporated herein by reference in its entirety, and the like. For example, it can be prepared by mixing the agent of the present invention and a desired antigen and, where necessary, emulsifying or dispersing the mixture, or adding the agent of the present invention to a vaccine containing a desired antigen and, where necessary, emulsifying or dispersing the mixture and the like.

The subject of administration of the vaccine of the present invention is not particularly limited as long as it is an animal having an immune system, and examples thereof include those recited as examples of the administration subject of the agent of the present invention.

The vaccine of the present invention may be administered by single administration or multiple successive administrations.

When the vaccine of the present invention is successively administered, the dosing period is not particularly limited and can be appropriately set according to, for example, the kind of antigen, subject of administration, administration form, administration route and the like. It is generally within the range of 1 to 90 days, preferably 1 to 30 days.

By administering the vaccine of the present invention to a target, allergy, infection, tumor and the like can be prevented or treated.

The present invention also provides a pharmaceutical composition containing compound (I) and α-cyclodextrin (hereinafter sometimes to be simply abbreviated as "the composition of the present invention").

While compound (I) to be contained in the composition of the present invention may be one similar to compound (I) contained in the agent of the present invention. Since α-cyclodextrin more remarkably exhibits the effects of improvement of dispersibility and improvement of the antigen-specific IgG1 subclass antibody production-enhancing effect, compound (I) wherein $R^3$ and $R^4$ are the same or different and each is a $C_{29-37}$ alkyl group is preferable. However, because of getting better results by addition of α-cyclodextrin, even if the composition of the present invention contains compound (I) and α-cyclodextrin, $R^3$ and $R^4$ are the same or different and each is a $C_{12-37}$ alkyl group, preferably a $C_{12-35}$ alkyl group. Particularly, a $C_{12-32}$ alkyl group is preferable, and a $C_{12-30}$ alkyl group is more preferable. Concretely, a $C_{12}$ alkyl group, $C_{13}$ alkyl group, $C_{14}$ alkyl group, $C_{15}$ alkyl group, $C_{16}$ alkyl group, $C_{17}$ alkyl group, $C_{19}$ alkyl group, $C_{19}$ alkyl group, $C_{20}$ alkyl group, $C_{21}$ alkyl group, $C_{22}$ alkyl group, $C_{23}$ alkyl group, $C_{24}$ alkyl group, $C_{25}$ alkyl group, $C_{26}$ alkyl group, $C_{27}$ alkyl group, $C_{26}$ alkyl group, $C_{29}$ alkyl group or $C_{30}$ alkyl group is more preferable. Since it is particularly superior in an IgG1 subclass antibody production-enhancing effect, a $C_{12-21}$ alkyl group or a $C_{26-30}$ alkyl group is particularly preferable. For example, a $C_{12}$ alkyl group, $C_{15}$ alkyl group, $C_{17}$ alkyl group, $C_{21}$ alkyl group or $C_{29}$ alkyl group is particularly preferable.

Preferable compound (I) to be contained in the composition of the present invention is compound (I) wherein $R^1$ and $R^2$ are the same or different and each is a $C_{1-3}$ alkyl group (e.g., methyl etc.), $R^3$ and $R^4$ are the same or different and each is a $C_{12-37}$ alkyl group, $X^1$ is —$NR^5$— wherein $R^5$ is a hydrogen atom or a $C_{1-6}$ alkyl group, and $X^2$ is —$NR^6$— wherein $R^6$ is a hydrogen atom or a $C_{1-6}$ alkyl group, more preferably compound (I) wherein $R^1$ and $R^2$ are each methyl, $R^3$ and $R^4$ are the same or different and each is a $C_{12-37}$ alkyl group, and $X^1$ and $X^2$ are each —NH—.

Still more preferable compound (I) to be contained in the composition of the present invention to achieve higher effectiveness is compound (I) wherein $R^1$ and $R^2$ are the same or different and each is a $C_{1-3}$ alkyl group (e.g., methyl etc.), $R^3$ and $R^4$ are the same or different and each is a $C_{29-37}$ alkyl group, $X^1$ is —$NR^5$— wherein $R^5$ is a hydrogen atom or a $C_{1-6}$ alkyl group, and $X^2$ is —$NR^6$— wherein $R^6$ is a hydrogen atom or a $C_{1-6}$ alkyl group.

More preferable compound (I) to be contained in the composition of the present invention is compound (I) wherein $R^1$ and $R^2$ are each methyl, $R^3$ and $R^4$ are the same or different and each is a $C_{29-37}$ alkyl group, and $X^1$ and $X^2$ are each —NH—.

Specific examples of preferable compound (I) to be contained in the composition of the present invention include N,N'-bis(hexadecanoyl)-L-cystine dimethyl ester,
N,N'-bis(2-heptylundecanoyl)-L-cystine dimethyl ester,
N,N'-bis[5,7,7-trimethyl-2-(1,3,3-trimethylbutyl)octanoyl]-L-cystine dimethyl ester,
N,N'-bis(tridecanoyl)-L-cystine dimethyl ester,
N,N'-bis(octadecanoyl)-L-cystine dimethyl ester,
N,N'-bis(triacontanoyl)-L-cystine dimethyl ester,
N,N'-bis(2-tetradecylhexadecanoyl)-L-cystine dimethyl ester,
N,N'-bis(2-octadecyleicosanoyl)-L-cystine dimethyl ester,
N,N'-bis(docosanoyl)-L-cystine dimethyl ester and the like, and further include, for higher effectiveness,
N,N'-bis(2-tetradecylhexadecanoyl)-L-cystine dimethyl ester,
N,N'-bis(2-octadecyleicosanoyl)-L-cystine dimethyl ester and the like.

As α-cyclodextrin to be contained in the composition of the present invention, those similar to α-cyclodextrin that may be contained in the agent of the present invention can be used.

While the content of compound (I) in the composition of the present invention is not particularly limited, it is preferably 0.1 to 99.9 wt %, more preferably 1 to 99 wt %.

While the content of α-cyclodextrin in the composition of the present invention is not particularly limited, it is preferably 0.005 to 20 wt %, more preferably 0.05 to 5 wt %.

While the weight ratio of the content of compound (I) and that of α-cyclodextrin (compound (I):α-cyclodextrin) in the composition of the present invention is not particularly limited, it is preferably 1:0.0002 to 2.0000, more preferably 1:0.002 to 0.2.

The composition of the present invention may contain a pharmacologically acceptable carrier in addition to compound (I) and α-cyclodextrin. Examples of the pharmacologically acceptable carrier that the composition of the present invention may contain include those similar to those exemplified as the pharmacologically acceptable carrier that the agent of the present invention may contain.

Examples of the dosage form of the composition of the present invention include those similar to those exemplified as the dosage form of the agent of the present invention.

The composition of the present invention can be produced by a method used conventionally in the technical field of preparation formulation, for example, the method described in the Japanese Pharmacopoeia, 16th Edition, which is incorporated herein by reference in its entirety, and the like.

Examples of the administration subject of the composition of the present invention include those recited as examples of the administration subject of the agent of the present invention.

The composition of the present invention may also be provided in the form of a kit wherein compound (I) and α-cyclodextrin are separately packaged.

Since the composition of the present invention has an antigen specific IgG1 subclass antibody production-enhancing effect (immunostimulatory effect) and may be used as, for example, an immunostimulating agent and the like.

Other features of the invention will become apparent in the course of the following descriptions of exemplary embodiments which are given for illustration of the invention and are not intended to be limiting thereof.

EXAMPLES

The reagents, apparatuses and materials used in the present invention are commercially available unless particularly indicated.

Synthesis Example 1

Synthesis of N,N'-bis(hexadecanoyl)-L-cystine dimethyl ester (SZ22)

To palmitic acid (900 mg, 3.51 mmol) were added N,N-dimethylformamide (7.4 mL) and L-cystine dimethyl ester hydrochloride (500 mg, 1.47 mmol) at room temperature, and the mixture was cooled in an ice bath. To the obtained mixture were added 1-ethyl-3-(3-dimethylaminopropyl)carbodiimide hydrochloride (673 mg, 3.51 mmol), 1-hydroxybenzotriazole monohydrate (538 mg, 3.51 mmol) and triethylamine (0.82 ml, 5.9 mmol), and the mixture was removed from the ice bath and stirred at room temperature. N,N-dimethylformamide (3.7 mL) was added at 1 hr and 2 hr from the start of stirring, and the mixture was further stirred at room temperature for 19 hr. 10% Aqueous citric acid solution (40 ml) was added to discontinue the reaction, and the mixture was extracted twice with toluene (200 ml). The combined organic layer was washed with saturated aqueous sodium hydrogen carbonate solution (40 ml) and 15% brine (30 ml), dried over anhydrous magnesium sulfate, and filtered. The filtrate was concentrated under reduced pressure and the obtained crude product was slurry-washed with hexane (20 ml) to give N,N'-bis(hexadecanoyl)-L-cystine dimethyl ester (874 mg, 1.17 mmol, yield 80%) as a white solid.

$^1$H-NMR (400 MHz, CDCl$_3$) δ: 0.88 (t, 3H, J=6.8 Hz), 1.25-1.30 (m, 24H), 1.64 (m, 2H), 2.25 (t, 2H, J=7.3 Hz), 3.19 (dd, 1H, J=5.1 Hz, 14.2 Hz), 3.22 (dd, 1H, J=5.1 Hz, 14.2 Hz), 3.77 (s, 3H), 4.88 (dt, 1H, J=7.4 Hz, 5.1 Hz), 6.40 (d, 1H, J=7.4 Hz).

ESIMS (m/z): 745.6 ([M+H]$^+$), 767.5 ([M+Na]$^+$), 783.5 ([M+K]$^+$).

Synthesis Example 2

Synthesis of N,N'-bis(2-heptylundecanoyl)-L-cystine dimethyl ester (SZ23)

To isostearic acid (999 mg, 3.51 mmol) were added N,N-dimethylformamide (9.8 mL) and L-cystine dimethyl ester hydrochloride (500 mg, 1.47 mmol) at room temperature, and the mixture was cooled in an ice bath. To the obtained mixture were added 1-ethyl-3-(3-dimethylaminopropyl)carbodiimide hydrochloride (673 mg, 3.51 mmol), 1-hydroxybenzotriazole monohydrate (538 mg, 3.51 mmol) and triethylamine (0.82 ml, 5.9 mmol), and the mixture was removed from the ice bath and stirred at room temperature for 20 hr. 10% Aqueous citric acid solution (30 ml) was added to discontinue the reaction, and the mixture was extracted with ethyl acetate (100 ml, 50 ml). The combined organic layer was washed with saturated aqueous sodium hydrogen carbonate solution (30 ml) and 15% brine (30 ml), dried over anhydrous magnesium sulfate, and filtered. The filtrate was concentrated under reduced pressure and the obtained crude product was slurry-washed with hexane (50 ml) to give N,N'-bis(2-heptylundecanoyl)-L-cystine dimethyl ester (738 mg, 0.92 mmol, yield 63%) as a pale-yellow solid.

$^1$H-NMR (400 MHz, CDCl$_3$) δ: 0.87 (m, 6H), 1.25-1.30 (m, 24H), 1.43 (m, 2H), 1.58 (m, 2H), 2.12 (m, 1H), 3.18 (dd, 1H, J=5.2 Hz, 14.1 Hz), 3.23 (dd, 1H, J=5.4 Hz, 14.1 Hz), 3.77 (s, 3H), 4.87 (dt, 1H, J=7.4 Hz, 5.3 Hz), 6.40 (d, 1H, J=7.4 Hz).

ESIMS (m/z): 801.6 ([M+H]$^+$), 823.6 ([M+Na]$^+$).

Synthesis Example 3

Synthesis of N,N'-bis[5,7,7-trimethyl-2-(1,3,3-trimethylbutyl)octanoyl]-L-cystine dimethyl ester (SZ23')

To 5,7,7-trimethyl-2-(1,3,3-trimethylbutyl)octanoic acid (1.14 ml, 3.52 mmol) were added N,N-dimethylformamide (9.8 mL) and L-cystine dimethyl ester hydrochloride (500 mg, 1.47 mmol) at room temperature, and the mixture was cooled in an ice bath. To the obtained mixture were added 1-ethyl-3-(3-dimethylaminopropyl)carbodiimide hydrochloride (673 mg, 3.52 mmol), 1-hydroxybenzotriazole monohydrate (538 mg, 3.52 mmol) and triethylamine (0.82 ml, 5.9 mmol), and the mixture was removed from the ice bath and stirred at room temperature for 18 hr. 10% Aqueous citric acid solution (50 ml) was added to discontinue the reaction, and the mixture was extracted twice with ethyl acetate (50 ml). The combined organic layer was washed with saturated aqueous sodium hydrogen carbonate solution (50 ml), water (50 ml) and 15% brine (50 ml), dried over anhydrous magnesium sulfate, and filtered. The filtrate was concentrated under reduced pressure and the obtained crude product was slurry-washed with hexane to give N,N'-bis[5,7,7-trimethyl-2-(1,3,3-trimethylbutyl)octanoyl]-L-cystine dimethyl ester (541 mg, 0.68 mmol, yield 46%) as a white solid.

$^1$H-NMR (400 MHz, CDCl$_3$) δ: 0.87-0.92 (m, 24H), 0.96-1.92 (m, 11H), 3.13-3.24 (m, 2H), 3.76 (s, 3H), 4.85-4.87 (m, 1H), 6.36-6.41 (m, 1H).

ESIMS (m/z): 801.8 ([M+H]$^+$), 823.9 ([M+Na]$^+$), 835.8 ([M+Cl]$^-$).

Synthesis Example 4

Synthesis of N,N'-bis(dodecanoyl)-L-cystine dimethyl ester (SZ24)

To lauric acid (705 mg, 3.52 mmol) were added N,N-dimethylformamide (9.8 mL) and L-cystine dimethyl ester hydrochloride (500 mg, 1.47 mmol) at room temperature, and the mixture was cooled in an ice bath. To the obtained mixture were added 1-ethyl-3-(3-dimethylaminopropyl)carbodiimide hydrochloride (675 mg, 3.52 mmol), 1-hydroxybenzotriazole (476 mg, 3.52 mmol) and triethylamine (0.82 ml, 5.9 mmol), and the mixture was removed from the ice bath and stirred at room temperature for 18 hr. 10% Aqueous citric acid solution (30 ml) was added to discontinue the reaction, and the mixture was extracted twice with ethyl acetate (100 ml). The combined organic layer was washed with saturated aqueous sodium hydrogen carbonate solution (40 ml) and 15% brine (20 ml), dried over anhydrous magnesium sulfate, and filtered. The filtrate was concentrated under reduced pressure and the obtained crude product was slurry-washed with ethyl acetate (20 ml) to give N,N'-bis(dodecanoyl)-L-cystine dimethyl ester (365 mg, 0.58 mmol, yield 39%) as a white solid.

$^1$H-NMR (400 MHz, CDCl$_3$) δ: 0.88 (t, 3H, J=6.9 Hz), 1.26-1.32 (m, 16H), 1.60-1.68 (m, 2H), 2.26 (t, 2H, J=7.6 Hz), 3.18 (dd, 1H, J=5.2 Hz, 14.2 Hz), 3.23 (dd, 1H, J=5.1 Hz, 14.2 Hz), 3.77 (s, 3H), 4.88 (dt, 1H, J=7.5 Hz, 5.1 Hz), 6.44 (d, 1H, J=7.4 Hz).

ESIMS (m/z): 633.2 ([M+H]$^+$), 655.3 ([M+Na]$^+$).

Synthesis Example 5

Synthesis of N,N'-bis(tridecanoyl)-L-cystine dimethyl ester (SZ34)

To tridecanoic acid (755 mg, 3.52 mmol) were added N,N-dimethylformamide (9.8 mL) and L-cystine dimethyl ester hydrochloride (500 mg, 1.47 mmol) at room temperature, and the mixture was cooled in an ice bath. To the obtained mixture were added 1-ethyl-3-(3-dimethylaminopropyl)carbodiimide hydrochloride (675 mg, 3.52 mmol), 1-hydroxybenzotriazole (476 mg, 3.52 mmol) and triethylamine (0.82 ml, 5.9 mmol), and the mixture was removed from the ice bath and stirred at room temperature for 17 hr. 10% Aqueous citric acid solution (30 ml) was added to discontinue the reaction, and the mixture was extracted with ethyl acetate (100 ml). The organic layer was washed twice with saturated aqueous sodium hydrogen carbonate solution (50 ml) and washed with 15% brine (20 ml), dried over anhydrous magnesium sulfate, and filtered. The filtrate was concentrated under reduced pressure and the obtained crude product was slurry-washed with ethyl acetate (20 ml) to give N,N'-bis(tridecanoyl)-L-cystine dimethyl ester (630 mg, 0.95 mmol, yield 65%) as a white solid.

$^1$H-NMR (400 MHz, CDCl$_3$) δ: 0.88 (t, 3H, J=6.9 Hz), 1.25-1.32 (m, 18H), 1.60-1.68 (m, 2H), 2.26 (t, 2H, J=7.6 Hz), 3.18 (dd, 1H, J=5.2 Hz, 14.2 Hz), 3.23 (dd, 1H, J=5.1 Hz, 14.2 Hz), 3.77 (s, 3H), 4.88 (dt, 1H, J=7.5 Hz, 5.1 Hz), 6.44 (d, 1H, J=7.4 Hz). ESIMS (m/z): 661.5 ([M+H]$^+$), 683.5 ([M+Na]$^+$).

Synthesis Example 6

Synthesis of N,N'-bis(octadecanoyl)-L-cystine dimethyl ester (SZ35)

To stearic acid (1.00 g, 3.52 mmol) were added N,N-dimethylformamide (9.8 mL) and L-cystine dimethyl ester hydrochloride (500 mg, 1.47 mmol) at room temperature, and the mixture was cooled in an ice bath. To the obtained mixture were added 1-ethyl-3-(3-dimethylaminopropyl)carbodiimide hydrochloride (675 mg, 3.52 mmol), 1-hydroxybenzotriazole (476 mg, 3.52 mmol) and triethylamine (0.82 ml, 5.9 mmol), and the mixture was removed from the ice bath and stirred at room temperature for 23 hr. 10% Aqueous citric acid solution (30 ml) was added to discontinue the reaction and then ethyl acetate (1000 ml) was added. The precipitate was collected by filtration. The filtered solid was washed with ethyl acetate (30 ml) to give N,N'-bis(octadecanoyl)-L-cystine dimethyl ester (543 mg, 0.68 mmol, yield 46%) as a white solid.

$^1$H-NMR (400 MHz, CDCl$_3$) δ: 0.88 (t, 3H, J=6.9 Hz), 1.25-1.34 (m, 28H), 1.60-1.68 (m, 2H), 2.26 (t, 2H, J=7.6 Hz), 3.17 (dd, 1H, J=5.1 Hz, 14.2 Hz), 3.23 (dd, 1H, J=5.1 Hz, 14.2 Hz), 3.82 (s, 3H), 4.87 (dt, 1H, J=7.4 Hz, 5.1 Hz), 6.42 (d, 1H, J=7.7 Hz). ESIMS (m/z): 801.6 ([M+H]$^+$), 835.5 ([M+Cl]$^-$).

Synthesis Example 7

Synthesis of N,N'-bis(triacontanoyl)-L-cystine dimethyl ester (SZ36)

To L-cystine dimethyl ester hydrochloride (100 mg, 0.29 mmol) were added 1,2-dichloroethane (2.9 mL) and melissic acid (319 mg, 0.70 mmol) at room temperature, and the mixture was cooled in an ice bath. To the obtained mixture were added 1-ethyl-3-(3-dimethylaminopropyl)carbodiimide hydrochloride (135 mg, 0.70 mmol), 1-hydroxybenzotriazole (95 mg, 0.70 mmol) and triethylamine (0.16 ml, 1.2 mmol), and the mixture was removed from the ice bath and stirred at 75° C. for 19.5 hr. The reaction mixture was filtered, and the filtered solid was washed with hexane/ethyl acetate (1/3), 10% aqueous citric acid solution, saturated aqueous sodium hydrogen carbonate solution and water to give N,N'-bis(triacontanoyl)-L-cystine dimethyl ester (229 mg, 0.20 mmol, yield 69%) as a pale-yellow solid. $^1$H-NMR (400 MHz, CDCl$_3$) δ: 0.88 (t, 3H, J=6.9 Hz), 1.25-1.38 (m, 52H), 1.59-1.64 (m, 2H), 2.37 (t, 2H, J=7.7 Hz), 3.17 (dd, 1H, J=5.5 Hz, 14.5 Hz), 3.24 (dd, 1H, J=5.1 Hz, 14.4 Hz), 3.82 (s, 3H), 4.92 (dt, 1H, J=7.4 Hz, 5.4 Hz), 6.94 (d, 1H, J=7.7 Hz). ESIMS (m/z): 1138.3 ([M+H]).

Synthesis Example 8

Synthesis of N,N'-bis(2-tetradecylhexadecanoyl)-L-cystine dimethyl ester (SZ37)

To L-cystine dimethyl ester hydrochloride (250.0 mg, 0.74 mmol) were added dichloromethane (4.9 mL) and 2-tetradecyl hexadecanoic acid (796.9 mg, 1.76 mmol) at room temperature, and the mixture was cooled in an ice bath. To the obtained mixture were added 1-ethyl-3-(3-dimethylaminopropyl)carbodiimide hydrochloride (337.4 mg, 1.76 mmol), 1-hydroxybenzotriazole (237.8 mg, 1.76 mmol), and triethylamine (0.41 ml, 2.94 mmol), and the mixture was removed from the ice bath and stirred at room temperature for 22 hr. 10% Aqueous citric acid solution (30 ml) was added to discontinue the reaction, and the mixture was extracted with dichloromethane (100 ml, 50 ml). The combined organic layer was washed twice with saturated aqueous sodium hydrogen carbonate solution (40 ml), and then washed with water (30 ml) and 15% brine (30 ml), dried over anhydrous magnesium sulfate, and filtered. The filtrate was concentrated under reduced pressure and the obtained crude product was slurry-washed with diethyl ether (20 ml) to give N,N'-bis(2-tetradecylhexadecanoyl)-L-cystine dimethyl ester (546.1 mg, 0.48 mmol, yield 65%) as a white solid.

$^1$H-NMR (400 MHz, CDCl3) δ: 0.88 (m, 6H), 1.25 (m, 48H), 1.40 (m, 2H), 1.60 (m, 2H), 2.11 (m, 1H), 3.16 (dd, 1H, J=5.2 Hz, 14.2 Hz), 3.24 (dd, 1H, J=5.5 Hz, 14.4 Hz), 3.77 (s, 3H), 4.86 (dt, 1H, J=5.4 Hz, 7.4 Hz), 6.40 (d, 1H, J=7.5 Hz).

ESIMS (m/z): 1138.2 ([M+H]+)

Synthesis Example 9

Synthesis of N,N'-bis(2-octadecyleicosanoyl)-L-cystine dimethyl ester (SZ38)

To L-cystine dimethyl ester hydrochloride (100.0 mg, 0.29 mmol) were added dichloromethane (2.0 mL) and 2-octadecyl eicosanoic acid (397.8 mg, 0.69 mmol) at room temperature, and the mixture was cooled in an ice bath. To the obtained mixture were added 1-ethyl-3-(3-dimethylaminopropyl)carbodiimide hydrochloride (135.0 mg, 0.69 mmol), 1-hydroxybenzotriazole (95.1 mg, 0.69 mmol) and triethylamine (0.16 ml, 1.16 mmol), and the mixture was removed from the ice bath and stirred at room temperature for 17 hr. 10% Aqueous citric acid solution (10 ml) was added to discontinue the reaction, and the mixture was extracted three times with dichloromethane (60 ml). The combined organic layer was washed twice with saturated aqueous sodium hydrogen carbonate solution (60 ml), and then washed with water (60 ml) and 15% brine (60 ml), dried over anhydrous magnesium sulfate, and filtered. The filtrate was concentrated under reduced pressure and the obtained crude product was slurry-washed with hexane (20 ml, 50 ml) to give N,N'-bis(2-octadecyleicosanoyl)-L-cystine dimethyl ester (262.0 mg, 0.19 mmol, yield 66%) as a white solid.

$^1$H-NMR (400 MHz, CDCl$_3$) δ: 0.88 (m, 6H), 1.25 (m, 64H), 1.42 (m, 2H), 1.63 (m, 2H), 2.12 (m, 1H), 3.16 (dd,

1H, J=5.2 Hz, 14.1 Hz), 3.24 (dd, 1H, J=5.4 Hz, 14.1 Hz), 3.76 (s, 3H), 4.86 (dt, 1H, J=7.4 Hz, 5.3 Hz), 6.40 (d, 1H, J=7.4 Hz).

ESIMS (m/z): 1362.4 ([M+H]+)

Synthesis Example 10

Synthesis of N,N'-bis(linoleoyl)-L-cystine dimethyl ester (SZ28)

To L-cystine dimethyl ester hydrochloride (500 mg, 1.47 mmol) were added N,N-dimethylformamide (9.8 mL) and linoleic acid (1.12 g, 3.51 mmol) at room temperature, and the mixture was cooled in an ice bath. Sequentially, 1-ethyl-3-(3-dimethylaminopropyl)carbodiimide hydrochloride (673 mg, 3.51 mmol), 1-hydroxybenzotriazole (538 mg, 3.51 mmol) and trimethylamine (0.82 ml, 5.86 mmol) were added, and the mixture was removed from the ice bath and stirred at room temperature for 20 hr. 10% Aqueous citric acid solution (30 ml) was added to discontinue the reaction, and the mixture was extracted twice with ethyl acetate (30 ml). The combined organic layer was washed with saturated aqueous sodium hydrogen carbonate solution (40 ml) and 15% brine (30 ml), dried over anhydrous magnesium sulfate, and filtered. The filtrate was concentrated under reduced pressure and the obtained crude product was purified by silica gel column chromatography (hexane/ethyl acetate), and recrystallized from hexane to give N,N'-bis(linoleoyl)-L-cystine dimethyl ester (450.4 mg, 0.57 mmol, yield 39%) as a white solid.

$^1$H-NMR (400 MHz, CDCl$_3$) δ: 0.89 (t, 3H, J=6.9 Hz), 1.27-1.37 (m, 14H), 1.64 (m, 2H), 2.05 (m, 4H), 2.26 (t, 2H, J=7.6 Hz), 2.77 (t, 2H, J=6.7 Hz), 3.18 (dd, 1H, J=5.2 Hz, 14.2 Hz), 3.23 (dd, 1H, J=5.0 Hz, 14.2 Hz), 3.77 (s, 3H), 4.88 (dt, 1H, J=7.4 Hz, 5.1 Hz), 5.28-5.42 (m, 4H), 6.39 (d, 1H, J=7.4 Hz).

ESIMS (m/z): 793.5 ([M+H]$^+$), 815.5 ([M+Na]$^+$).

Synthesis Example 11

Synthesis of N,N'-bis(docosanoyl)-L-cystine dimethyl ester (SZ66)

To L-cystine dimethyl ester hydrochloride (250 mg, 0.73 mmol) were added N,N-dimethylformamide (5 mL) and behenic acid (597 mg, 1.75 mmol) at room temperature, and the mixture was cooled in an ice bath. To the obtained mixture were added 1-ethyl-3-(3-dimethylaminopropyl)carbodiimide hydrochloride (336 mg, 1.75 mmol), 1-hydroxybenzotriazole (237 mg, 1.75 mmol) and triethylamine (0.41 ml, 2.92 mmol), and the mixture was removed from the ice bath and stirred at room temperature for 20.5 hr. To the reaction mixture was added ethyl acetate (50 ml) and the mixture was filtered, and the filtered solid was slurry-washed with ethyl acetate/hexane (1/1, 50 ml). After that, the obtained solid was dissolved in ethyl acetate (100 ml), washed with 10% aqueous citric acid solution (50 ml) and water, and the organic layer was concentrated. The obtained solid was slurry-washed again with ethyl acetate/hexane (3/2, 40 ml) to give N,N'-bis(docosanoyl)-L-cystine dimethyl ester (307 mg, 0.34 mmol, yield 46%) as a white solid.

$^1$H-NMR (400 MHz, CDCl$_3$) δ: 0.88 (t, 3H, J=6.8 Hz), 1.25 (m, 36H), 1.62 (m, 2H), 2.25 (t, 2H, J=7.6 Hz), 3.18 (dd, 1H, J=5.2 Hz, 14.4 Hz), 3.23 (dd, 1H, J=5.2 Hz, 14.2 Hz), 3.77 (s, 3H), 4.87 (dt, 1H, J=5.2 Hz, 7.5 Hz), 6.40 (d, 1H, J=7.2 Hz).

ESIMS (m/z): 913.7 ([M+H]$^+$).

(2) Adjuvant Activity Test

Example 1

Evaluation Test of Adjuvant Activity of N,N'-bis(2-heptylundecanoyl)-L-cystine dimethyl ester (SZ23)

8-Week-old female BALB/c mice were divided into groups (N=6), and each group was primarily immunized by dorsal-subcutaneous administration of (1) ovalbumin (OVA) (10 μg) dissolved in saline as an antigen (OVA single administration group), (2) OVA (10 μg) and, as an adjuvant, N,N'-bis(2-heptylundecanoyl)-L-cystine dimethyl ester (SZ23) (2.56 μmol) (corresponding to 0.2 mg based on aluminum hydroxide gel adjuvant) dissolved in saline (SZ23 addition group), (3) OVA (10 μg) and cystine dimethyl ester ((CyssOMe)$_2$) (2.56 μmol) dissolved in saline (cystine dimethyl ester addition group), (4) OVA (10 μg) and isostearic acid (ISA) (5.12 μmol) dissolved in saline (isostearic acid addition group), and (5) OVA (10 μg), (CyssOMe)$_2$ (2.56 μmol) and ISA (5.12 μmol) dissolved in saline (cystine dimethyl ester-isostearic acid mixture addition group), each per mouse. One week later, the secondary immunization was carried out by dorsal-subcutaneous administration of solutions similar to those of the above-mentioned (1) to (5) again. Two weeks from the secondary immunization, the whole blood and spleen were extracted under anesthesia, and the obtained serum sample was measured for anti OVA-specific IgG1 subclass antibody. A method for measurement of the anti OVA-specific IgG1 subclass antibody in Example 1, and the following Examples 2, 4, 7 to 10 and 13 to 16 is as follows.

Measurement Method of Anti OVA-Specific IgG1 Subclass Antibody

To a 96 well plate was added 5 μg/ml OVA at 100 μl/well, and the mixture was incubated at 4° C. overnight. After incubation, the mixture was washed three times with 200 μl of PBS-T (PBS (phosphate buffered saline)+0.05% (v/v) Tween 20) per well, and blocked with 100 μl of 5% FCS (fatal calf serum)/PBS solution per well at room temperature for 1 to 2 hr. Thereafter, the mixture was washed three times with PBS-T (200 μl/well), a diluted serum sample (100 μl/well) or the same amount of 5% FCS/PBS solution as a control was added, and the mixture was incubated at 37° C. for 1 hr. Thereafter, the mixture was washed five times with PBS-T (200 μl/well), a diluted biotinylated anti-mouse IgG1 antibody (100 μl/well) was added, and the mixture was incubated at 37° C. for 45 min. Thereafter, the mixture was washed five times with PBS-T (200 μl/well), a diluted anti-biotin-HRP antibody was added (100 μl/well), and the mixture was incubated at 37° C. for another 30 min. Thereafter, the mixture was washed five times with PBS-T (200 μl/well), TMB substrate solution was added (100 μl/well), and the mixture was incubated at room temperature for 10 to 15 min. Thereafter, a reaction quenching liquid (2N sulfuric acid solution) was added (50 μl/well) to discontinue a color developing reaction, and the absorbance (OD Value=450 nm) was measured by a microplate reader.

The results are shown in FIG. 1.

As is clear from the results shown in FIG. 1, production of anti OVA-specific IgG1 subclass antibody significantly increased in the SZ23 addition group (in Figure: SZ23) as compared to that of the OVA single administration group (in Figure: OVA). The result confirms that N,N'-bis(2-heptylundecanoyl)-L-cystine dimethyl ester (SZ23) has an adjuvant activity. The productions of anti OVA-specific IgG1 subclass antibody in the cystine dimethyl ester addition group (in Figure: (CyssOMe)$_2$), the isostearic acid addition group (in Figure: ISA), and the cystine dimethyl ester-isostearic acid mixture addition group (in Figure: ISA+(CyssOMe)$_2$) did not show a significant difference from that in the OVA single administration group. The result reveals that N,N'-bis(2-heptylundecanoyl)-L-cystine dimethyl ester (SZ23) obtained by condensing cystine dimethyl ester and isostearic acid has an adjuvant activity.

Example 2

Evaluation Test of Adjuvant Activity of N,N'-bis(2-heptylundecanoyl)-L-cystine dimethyl ester (SZ23)

8-Week-old female BALB/c mice were divided into groups (N=6), and each group was primarily immunized by dorsal-subcutaneous administration of (1) ovalbumin (OVA) (10 µg) dissolved in saline as an antigen (OVA single administration group), (2) OVA (10 µg) and, as an adjuvant, N,N'-bis(2-heptylundecanoyl)-L-cystine dimethyl ester (SZ23) (2.56 µmol) (corresponding to 0.2 mg based on aluminum hydroxide gel adjuvant) dissolved in saline (SZ23; 2.56 µmol addition group), (3) OVA (10 µg) and SZ23; 0.256 µmol dissolved in saline (SZ23; 0.256 µmol addition group), (4) OVA (10 µg) and SZ23; 0.0256 µmol dissolved in saline (SZ23; 0.0256 µmol addition group), (5) OVA (10 µg) and aluminum hydroxide gel adjuvant (2.56 µmol) (0.2 mg) dissolved in saline (ALUM addition group, positive control), and (6) saline (saline single administration group), per each mouse. One week later, the secondary immunization was carried out by dorsal-subcutaneous administration of solutions similar to those of the abovementioned (1) to (6) again. Two weeks from the secondary immunization, the whole blood and spleen were extracted under anesthesia, and the obtained serum sample was measured for anti OVA-specific IgG1 subclass antibody. The results are shown in FIG. 2.

Figure 2:
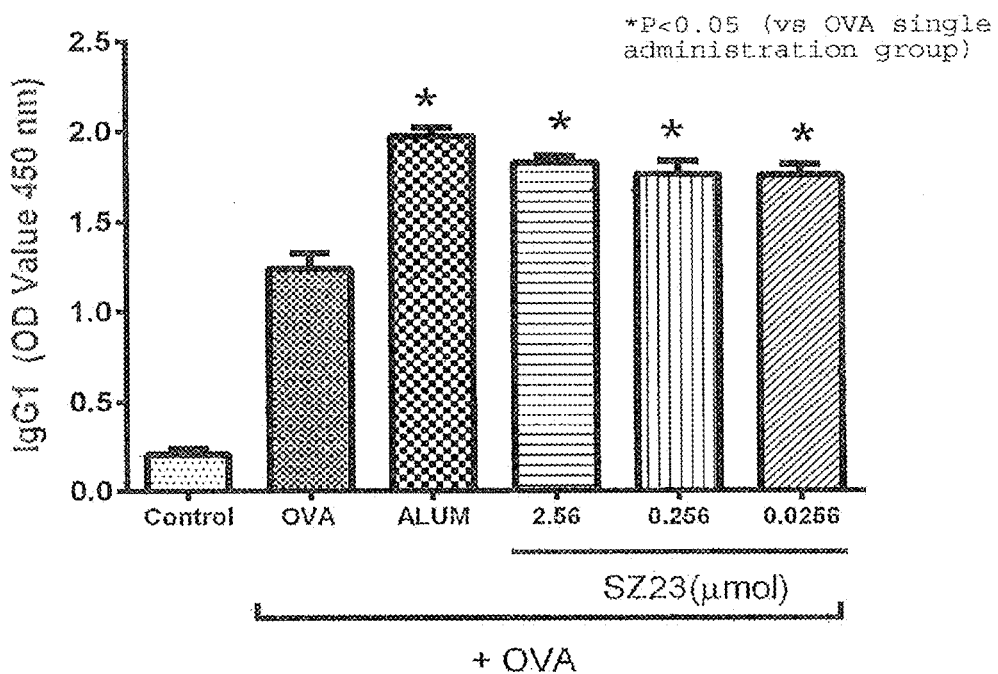
FIG. 2 is a graph showing the results of the evaluation test of adjuvant activity of N,N'-bis(2-heptylundecanoyl)-L-cystine dimethyl ester (SZ23: compound wherein the group corresponding to $R^3$ and $R^4$ in the formula (I) is $C_{17}$ alkyl group) in Example 2, wherein "Control" shows saline single administration group, "OVA" shows OVA single administration group, "ALUM" shows aluminum hydroxide gel adjuvant addition group, "2.56" shows SZ23; 2.56 μmol addition group, "0.256" shows SZ23; 0.256 μmol addition group, and "0.0256" shows SZ23; 0.0256 μmol addition group.

As is clear from the results shown in FIG. 2, production of anti OVA-specific IgG1 subclass antibody in all addition groups of SZ23; 2.56 µmol, 0.256 µmol and 0.0256 µmol (in Figure: 2.56, 0.256 and 0.0256) significantly increased as compared to that of the OVA single administration group (in Figure: OVA), and was of the same level as that of the ALUM addition group (in Figure: ALUM). These results confirm that N,N'-bis(2-heptylundecanoyl)-L-cystine dimethyl ester (SZ23) has an adjuvant activity of the same level as that of aluminum hydroxide gel adjuvant.

Example 3

Evaluation Test of Allergy Induction Activity of N,N'-bis(2-heptylundecanoyl)-L-cystine dimethyl ester (SZ23)

The serum sample obtained in Example 2 was measured for an anti OVA-specific IgE antibody. The measurement method of the anti OVA-specific IgE antibody is as follows.
Measurement Method of Anti OVA-Specific IgE Antibody DS mouse IgE ELISA (OVA) kit manufactured by DS Pharma Biomedical Co., Ltd. was used. The protocol is briefly shown below.

The serum sample and a standard reagent for drawing an analytical curve were diluted with a buffer and, after stirring, left standing at room temperature for 10 min. The sample and the standard solution were added to a plate bound with an IgE capture antibody in advance and, after stirring, the mixture was left standing at room temperature for 60 min. The mixture was washed three times with wash, HRP-labeled OVA was added, and the mixture was left standing at room temperature for 30 min. The mixture was washed three times with wash, a substrate solution was added, and the mixture was left standing in dark at room temperature for 30 min. A reaction quenching liquid was added, the mixture was stirred, and the absorbance (OD Value=450 nm) was immediately measured.

Figure 3:
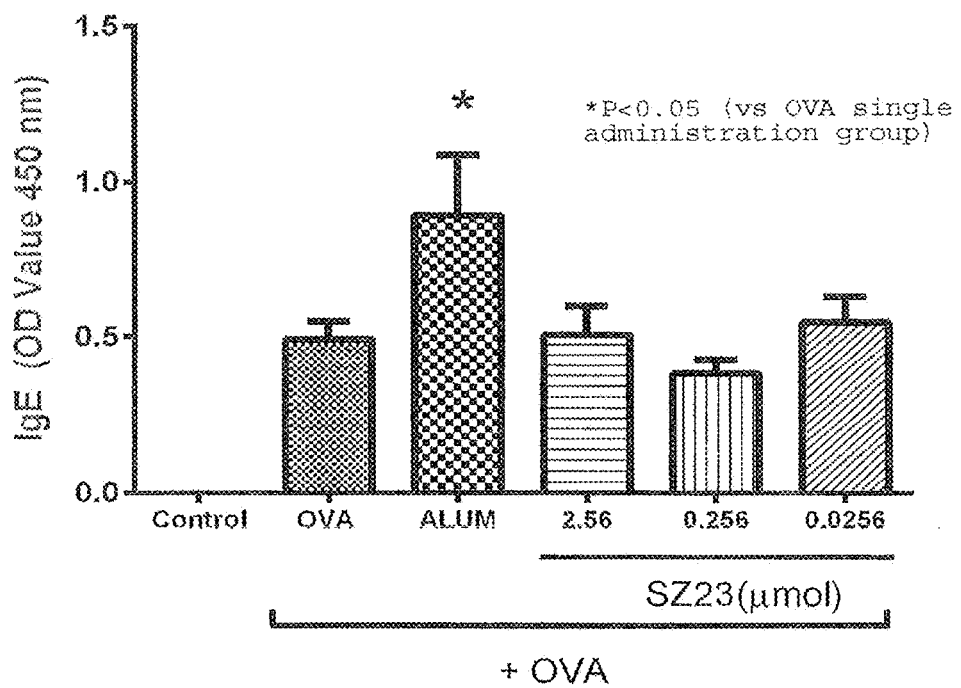
FIG. 3 is a graph showing the results of the evaluation test of allergy inducing activity of N,N'-bis(2-heptylundecanoyl)-L-cystine dimethyl ester (SZ23: compound wherein the group corresponding to $R^3$ and $R^4$ in the formula (I) is $C_{17}$ alkyl group) in Example 3, wherein "Control" shows saline single administration group, "OVA" shows OVA single administration group, "ALUM" shows aluminum hydroxide gel adjuvant addition group, "2.56" shows SZ23; 2.56 μmol addition group, "0.256" shows SZ23; 0.256 μmol addition group, and "0.0256" shows SZ23; 0.0256 μmol addition group.

The results are shown in FIG. 3.

As is clear from the results shown in FIG. 3, production of anti OVA-specific IgE antibody significantly increased in the ALUM addition group (in Figure: ALUM) as compared to that of the OVA single administration group (in Figure: OVA) as previously reported. In contrast, an increase in the production of anti OVA-specific IgE antibody was not observed in all of the SZ23; 2.56 µmol, 0.256 µmol and 0.0256 µmol addition groups (in Figure: 2.56, 0.256 and 0.0256). The results have clarified that N,N'-bis(2-heptylundecanoyl)-L-cystine dimethyl ester (SZ23) shows a lower allergy inducing activity as compared to aluminum hydroxide gel adjuvant that problematically induces allergy by inoculation.

Example 4

Comparison Test of Adjuvant Activity of N,N'-bis (2-heptylundecanoyl)-L-cystine dimethyl ester (SZ23) and N,N'-bis(dodecanoyl)-L-cystine dimethyl ester (SZ24)

8-Week-old female BALB/c mice were divided into groups (N=6), and each group was primarily immunized by dorsal-subcutaneous administration of (1) ovalbumin (OVA) (10 µg) dissolved in saline as an antigen (OVA single administration group), (2) OVA (10 µg) and, as an adjuvant, N,N'-bis(2-heptylundecanoyl)-L-cystine dimethyl ester (SZ23) (2.56 µmol) dissolved in saline (SZ23 addition group), (3) OVA (10 µg) and N,N'-bis(dodecanoyl)-L-cystine dimethyl ester (SZ24) (2.56 µmol) dissolved in saline (SZ24 addition group), and (4) saline (saline single administration group), each per mouse. One week later, the secondary immunization was carried out by dorsal-subcutaneous administration of solutions similar to those of the above-mentioned (1) to (4) again. Two weeks from the secondary immunization, the whole blood was extracted under anesthesia, and the obtained serum sample was measured for anti OVA-specific IgG1 subclass antibody. SZ24 is disclosed in JP-A-4-230359, which is incorporated herein by reference in its entirety. The results are shown in FIG. 4.

Figure 4:
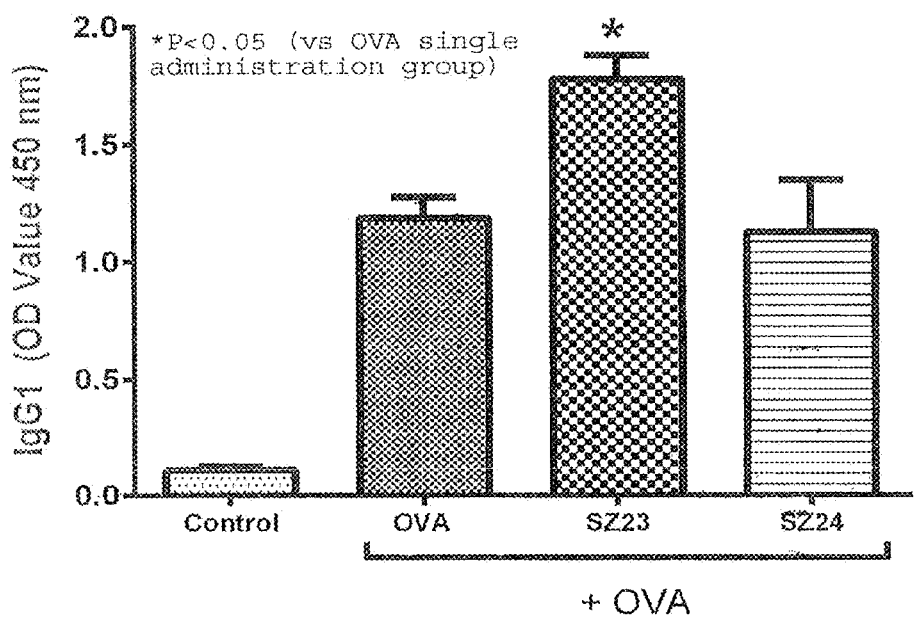
FIG. 4 is a graph showing the results of the comparison test of adjuvant activity between N,N'-bis(2-heptylundecanoyl)-L-cystine dimethyl ester (SZ23: compound wherein the group corresponding to $R^3$ and $R^4$ in the formula (I) is $C_{17}$ alkyl group) and N,N'-bis(dodecanoyl)-L-cystine dimethyl ester (SZ24: compound wherein the group corresponding to $R^3$ and $R^4$ in the formula (I) is $C_{11}$ alkyl group) in Example 4, wherein "Control" shows saline single administration group, "OVA" shows OVA single administration group, "SZ23" shows SZ23 addition group, and "SZ24" shows SZ24 addition group.

As is clear from the results shown in FIG. 4, production of anti OVA-specific IgG1 subclass antibody significantly increased in the SZ23 addition group (in Figure: SZ23) as compared to that of the OVA single administration group (in Figure: OVA). On the other hand, production of anti OVA-specific IgG1 subclass antibody in the SZ24 addition group (in Figure: SZ24) did not show a significant difference from that in the OVA single administration group. The results show that N,N'-bis(2-heptylundecanoyl)-L-cystine dimethyl ester (SZ23) of the present invention has a higher adjuvant activity than known N,N'-bis(dodecanoyl)-L-cystine dimethyl ester (SZ24).

Example 5

Evaluation Test of Immunostimulatory Effect of N,N'-bis(2-heptylundecanoyl)-L-cystine dimethyl ester (SZ23) on Human Monocyte Cell Line Human monocyte cell line THP-1 was seeded on a 96 well plate at a concentration of $3.0 \times 10^5$ cells/ml, and incubated under the conditions of 37° C., 5% $CO_2$ for 3 hr. N,N'-bis(2-heptylundecanoyl)-L-cystine dimethyl ester (SZ23) was added at a final concentration of 4 nM, 400 nM or 4 µM, and the mixture was cultured for 24 hr. For culture of THP-1, RPMI-1640 added with FBS (final concentration 10%), penicillin (final concentration 100 U/ml), streptomycin (final concentration 100 µg/ml) was used as a maintenance medium. The cells were passaged once every 3 days. After culture for 24 hr, CCK-8 reagent (cell counting kit-8, manufactured by DOJINDO LABORATORIES) was added to each well by 10 µl, and the mixture was incubated under the conditions of 37° C., 5% $CO_2$ for 2 hr, after which the absorbance (OD Value=450 nm) was measured by a microplate reader. The absorbance of each well divided by the absorbance of a well added only with a medium was defined as Stimulation Index (SI), and cell proliferation was evaluated using SI. The results are shown in FIG. 5.

Figure 5:
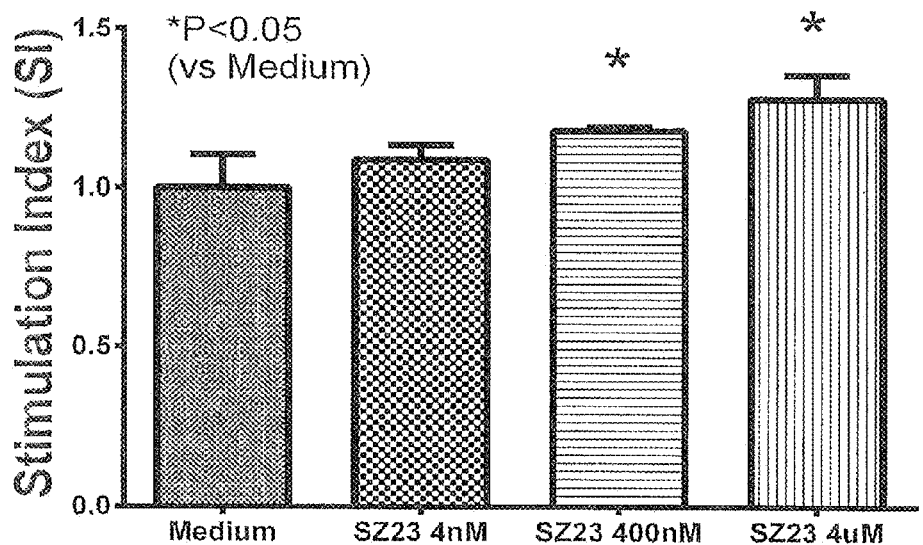
FIG. 5 is a graph showing the results of the evaluation test of immunostimulatory effect of N,N'-bis(2-heptylundecanoyl)-L-cystine dimethyl ester (SZ23: compound wherein the group corresponding to R³ and R⁴ in the formula (I) is C₁₇ alkyl group) on human monocytic cell line in Example 5.

As is clear from results shown in FIG. 5, a significant cell proliferation was found in the wells added with N,N'-bis(2-heptylundecanoyl)-L-cystine dimethyl ester at a final concentration of 400 nM, 4 µM (In Figure: SZ23 400 nM, SZ23 4 µM) as compared to the well added only with a medium (In Figure: Medium). The results suggest that N,N'-bis(2-heptylundecanoyl)-L-cystine dimethyl ester (SZ23) has an action to promote the growth of and activate monocytic cell.

Example 6

Evaluation Test of Immunostimulatory Effect of N,N'-bis(2-heptylundecanoyl)-L-cystine dimethyl ester (SZ23) on Mouse Macrophage-Like Cell Line (RAW)

Mouse macrophage-like cell line RAW was seeded on a 96 well plate at a concentration of $3.0 \times 10^5$ cells/ml, and incubated under the conditions of 37° C., 5% $CO_2$ for 3 hr. N,N'-bis(2-heptylundecanoyl)-L-cystine dimethyl ester (SZ23) was added at a final concentration of 4 nM, 400 nM or 4 µM, and the mixture was cultured for 24 hr. For culture of RAW, DMEM (High Glucose) added with FBS (final concentration 10%), penicillin (final concentration 100 U/ml), streptomycin (final concentration 100 µg/ml) was used as a maintenance medium. The cells were passaged once every 3 days. After culture for 24 hr, CCK-8 reagent (cell counting kit-8, manufactured by DOJINDO LABORATORIES) was added to each well by 10 µl, and the mixture was incubated under the conditions of 37° C., 5% $CO_2$ for 2 hr, after which absorbance (450 nm) was measured by a microplate reader. The absorbance of each well divided by the absorbance of a well added only with a medium was defined as Stimulation Index (SI) as in Example 5, and cell proliferation was evaluated using SI. The results are shown in FIG. 6.

Figure 6:
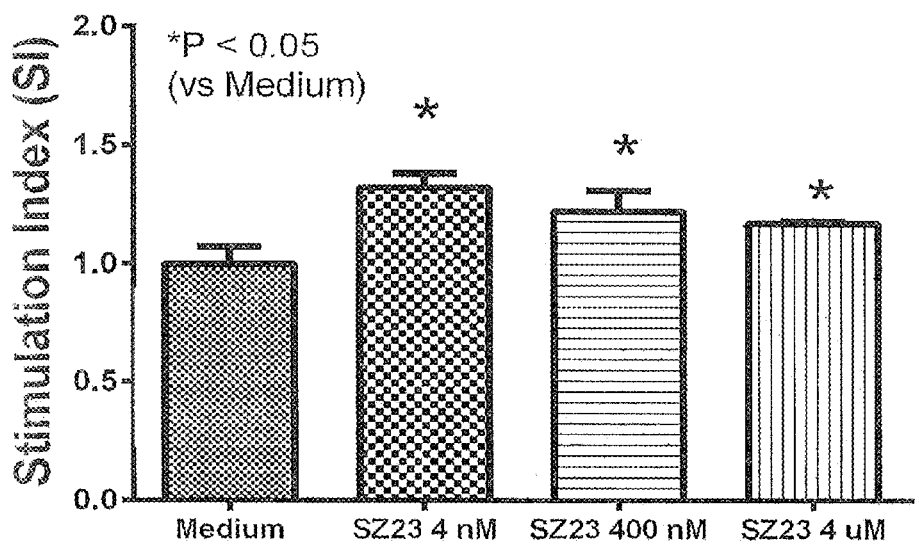
FIG. 6 is a graph showing the results of the evaluation test of immunostimulatory effect of N,N'-bis(2-heptylundecanoyl)-L-cystine dimethyl ester (SZ23: compound wherein the group corresponding to R³ and R⁴ in the formula (I) is C₁₇ alkyl group) on mouse macrophage-like cell line (RAW) in Example 6.

As is clear from results shown in FIG. 6, a significant cell proliferation was found in the wells added with N,N'-bis(2-heptylundecanoyl)-L-cystine dimethyl ester at a final concentration of 4 nM, 400 nM, 4 µM (In Figure: 4 nM, 400 nM, 4 µM) as compared to the well added only with a medium (In Figure: Medium). The results suggest that N,N'-bis(2-heptylundecanoyl)-L-cystine dimethyl ester (SZ23) has an action to promote the growth of and activate macrophage.

Example 7

Evaluation Test of Adjuvant Activity of N,N'-bis(hexadecanoyl)-L-cystine dimethyl ester (SZ22)

This test was performed in the same manner as in Example 4 except N,N'-bis(hexadecanoyl)-L-cystine dimethyl ester (SZ22) was used instead of N,N'-bis(dodecanoyl)-L-cystine dimethyl ester (SZ24). The results are shown in FIG. 7.

Figure 7:
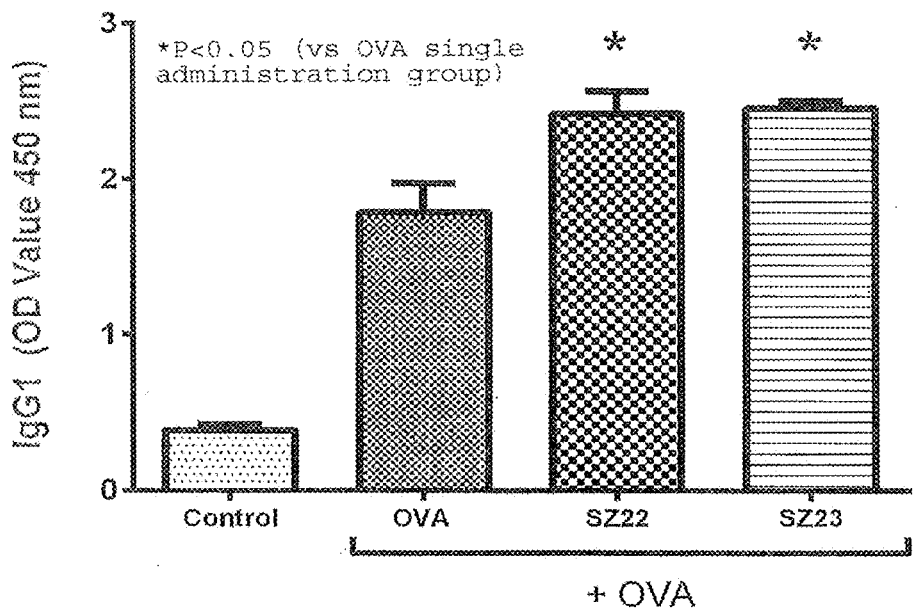
FIG. 7 is a graph showing the results of the evaluation test of adjuvant activity of N,N'-bis(hexadecanoyl)-L-cystine dimethyl ester (SZ22: compound wherein the group corresponding to R³ and R⁴ in the formula (I) is C₁₅ alkyl group) in Example 7, wherein "Control" shows saline single administration group, "OVA" shows OVA single administration group, "SZ22" shows SZ22 addition group, and "SZ23" shows SZ23 addition group.

As is clear from results shown in FIG. 7, production of anti OVA-specific IgG1 subclass antibody significantly increased in the SZ23 addition group (In Figure: SZ23) and the SZ22 addition group (In Figure: SZ22), as compared to that of the OVA single administration group (In Figure: OVA). The results reveal that N,N'-bis(hexadecanoyl)-L-cystine dimethyl ester (SZ22) also has an adjuvant activity as does N,N'-bis(2-heptylundecanoyl)-L-cystine dimethyl ester (SZ23).

Example 8

Evaluation Test of Adjuvant Activity of N,N'-bis(tridecanoyl)-L-cystine dimethyl ester (SZ34), N,N'-bis(octadecanoyl)-L-cystine dimethyl ester (SZ35) and N,N'-bis(triacontanoyl)-L-cystine dimethyl ester (SZ36)

This test was performed in the same manner as in Example 4 except N,N'-bis(tridecanoyl)-L-cystine dimethyl ester (SZ34), N,N'-bis(octadecanoyl)-L-cystine dimethyl ester (SZ35) and N,N'-bis(triacontanoyl)-L-cystine dimethyl ester (SZ36) were used instead of N,N'-bis(dodecanoyl)-L-cystine dimethyl ester (SZ24). The results are shown in FIG. 8.

Figure 8:
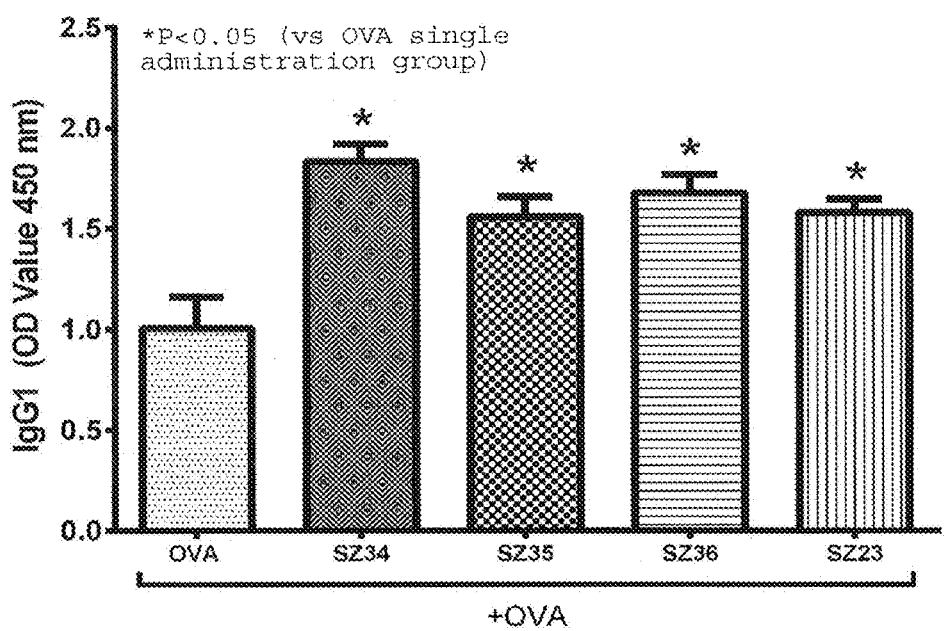
FIG. 8 is a graph showing the results of the evaluation test of adjuvant activity of N,N'-bis(tridecanoyl)-L-cystine dimethyl ester (SZ34: compound wherein the group corresponding to R³ and R⁴ in the formula (I) is C₁₂ alkyl group), N,N'-bis(octadecanoyl)-L-cystine dimethyl ester (SZ35: compound wherein the group corresponding to R³ and R⁴ in the formula (I) is C₁₇ alkyl group) and N,N'-bis(triacontanoyl)-L-cystine dimethyl ester (SZ36: compound wherein the group corresponding to R³ and R⁴ in the formula (I) is C₂₉ alkyl group) in Example 8, wherein "OVA" shows OVA single administration group, "SZ34" shows SZ34 addition group, "SZ35" shows SZ35 addition group, "SZ36" shows SZ36 addition group, and "SZ23" shows SZ23 addition group.

As is clear from the results shown in FIG. 8, the SZ34 addition group (in Figure: SZ34), production of anti OVA-specific IgG1 subclass antibody significantly increased in the SZ35 addition group (in Figure: SZ35) and the SZ36 addition group (in Figure: SZ36) as compared to that of the OVA single administration group (in Figure: OVA). The results reveal that N,N'-bis(tridecanoyl)-L-cystine dimethyl ester (SZ34), N,N'-bis(octadecanoyl)-L-cystine dimethyl ester (SZ35) and N,N'-bis(triacontanoyl)-L-cystine dimethyl ester (SZ36) also have an adjuvant activity as does N,N'-bis(2-heptylundecanoyl)-L-cystine dimethyl ester (SZ23).

Example 9

Evaluation Test of Adjuvant Activity of N,N'-bis[5,7,7-trimethyl-2-(1,3,3-trimethylbutyl)octanoyl]-L-cystine dimethyl ester (SZ23')

This test was performed in the same manner as in Example 4 except N,N'-bis[5,7,7-trimethyl-2-(1,3,3-trimethylbutyl)octanoyl]-L-cystine dimethyl ester (SZ23') was used instead of N,N'-bis(dodecanoyl)-L-cystine dimethyl ester (SZ24). The results are shown in FIG. 9.

Figure 9:
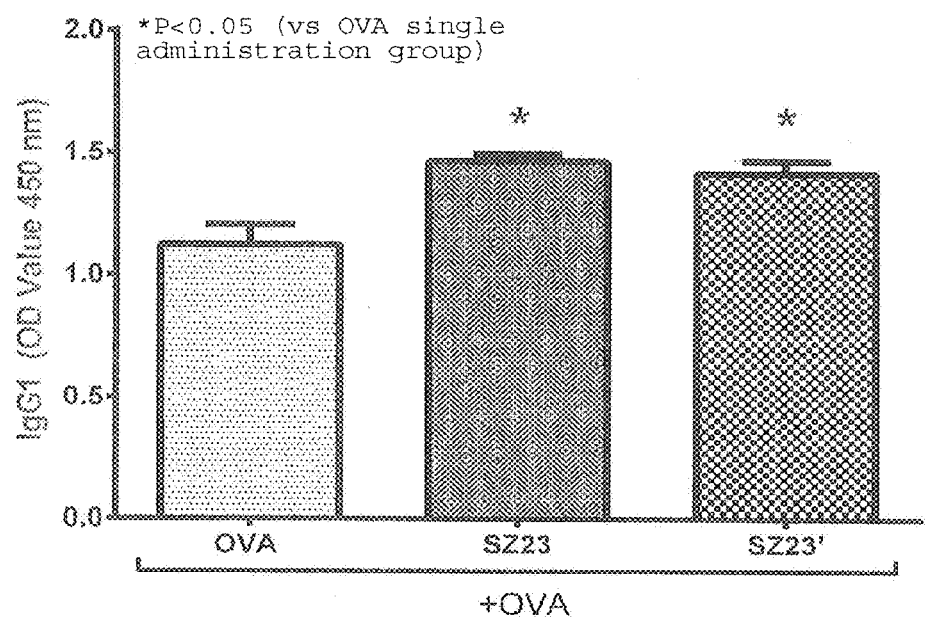
FIG. 9 is a graph showing the results of the evaluation test of adjuvant activity of N,N'-bis[5,7,7-trimethyl-2-(1,3,3-trimethylbutyl)octanoyl]-L-cystine dimethyl ester (SZ23': compound wherein the group corresponding to R³ and R⁴ in the formula (I) is C₁₇ alkyl group) in Example 9, wherein "OVA" shows OVA single administration group, "SZ23" shows SZ23 addition group, and "SZ23'" shows SZ23' addition group.

As is clear from the results shown in FIG. 9, production of anti OVA-specific IgG1 subclass antibody significantly increased in the SZ23' addition group as compared that of the OVA single administration group (in Figure: OVA). The results reveal that N,N'-bis[5,7,7-trimethyl-2-(1,3,3-trimethylbutyl)octanoyl]-L-cystine dimethyl ester (SZ23') also has an adjuvant activity as does N,N'-bis(2-heptylundecanoyl)-L-cystine dimethyl ester (SZ23).

Example 10

Evaluation Test of Adjuvant Activity of N,N'-bis(linoleoyl)-L-cystine dimethyl ester (SZ28) and N,N'-bis(octadecanoyl)-L-cystine dimethyl ester (SZ35)

This test was performed in the same manner as in Example 4 except N,N'-bis(linoleoyl)-L-cystine dimethyl ester (SZ28) and N,N'-bis(octadecanoyl)-L-cystine dimethyl ester (SZ35) were used instead of N,N'-bis(2-heptylundecanoyl)-L-cystine dimethyl ester (SZ23) and N,N'-bis(dodecanoyl)-L-cystine dimethyl ester (SZ24). The results are shown in FIG. 10.

Figure 10:
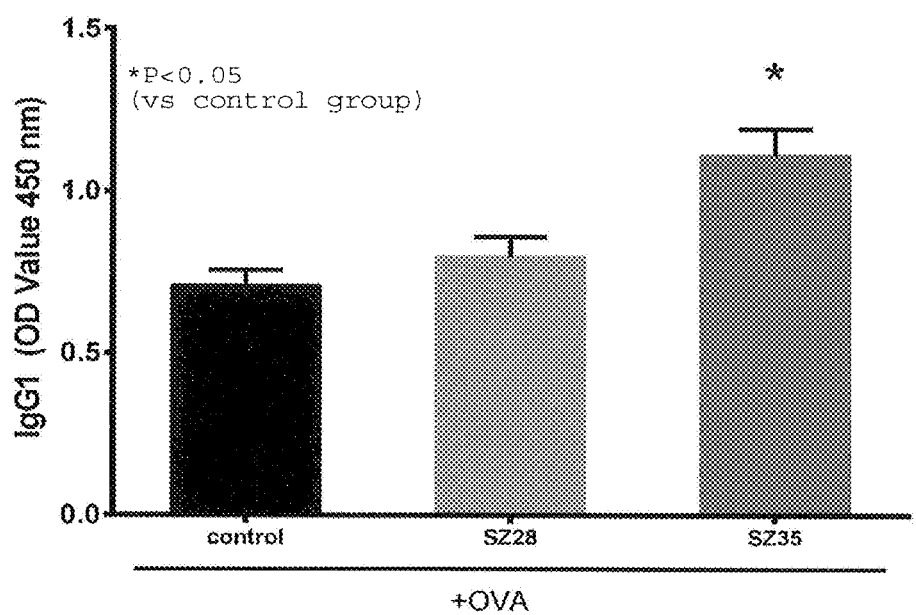
FIG. 10 is a graph showing the results of the evaluation test of adjuvant activity of N,N'-bis(linoleoyl)-L-cystine dimethyl ester (SZ28: compound wherein the group corresponding to R³ and R⁴ in the formula (I) is C₁₇ alkenyl group) and N,N'-bis(octadecanoyl)-L-cystine dimethyl ester (SZ35: compound wherein the group corresponding to R³ and R⁴ in the formula (I) is C₁₇ alkyl group) in Example 10, wherein "control" shows OVA single administration group.

As is clear from the results shown in FIG. 10, production of anti OVA-specific IgG1 subclass antibody significantly increased in the SZ35 addition group (in Figure: SZ35) as compared to that of the OVA single administration group (in Figure: control), but production of anti OVA-specific IgG1 subclass antibody did not increase significantly in the SZ28 addition group as compared to that of the OVA single administration group (in Figure: control). The results reveal that N,N'-bis(octadecanoyl)-L-cystine dimethyl ester (SZ35) has a higher adjuvant activity than N,N'-bis(linoleoyl)-L-cystine dimethyl ester (SZ28).

(3) Dispersibility Investigation Test

Example 11

Dispersibility Investigation Test of N,N'-bis(2-tetradecylhexadecanoyl)-L-cystine dimethyl ester (SZ37) and N,N'-bis(2-octadecyleicosanoyl)-L-cystine dimethyl ester (SZ38)

N,N'-bis(2-tetradecylhexadecanoyl)-L-cystine dimethyl ester (SZ37) and N,N'-bis(2-octadecyleicosanoyl)-L-cystine dimethyl ester (SZ38) (0.256 µmol) were each dispensed to a 2 mL tube containing zirconia beads, saline or 5% α-cyclodextrin (hereinafter to be also simply referred to as αCD)-added saline (1 mL) was added, and the mixture was stirred. The absorbance (OD Value=650 nm) was measured by a microplate reader, and the turbidity was calculated as an index of dispersibility. The measurement method of the turbidity is as follows.
Method for Measurement of Turbidity SZ37 and SZ38 (0.256 µmol) were each dispensed to a 2 mL tube containing zirconia beads, saline or 5% αCD-added saline (1 mL) was added, and the mixture was vigorously stirred three times under conditions of 3.15 seconds one time at 6000 rpm. The mixture was dispensed by 200 µL to a 96 well plate, and the absorbance (OD Value=650 nm) was measured by a microplate reader. As a control, kaolinite (1 mg) was dissolved in distilled water (1 L), and the absorbance (OD Value=650 nm) was measured by a microplate reader. The absorbance thereof (OD Value=650 nm) was defined to be turbidity: 1, and the turbidity of each sample was calculated from the ratio with the measured value of kaolinite.

Figure 11:
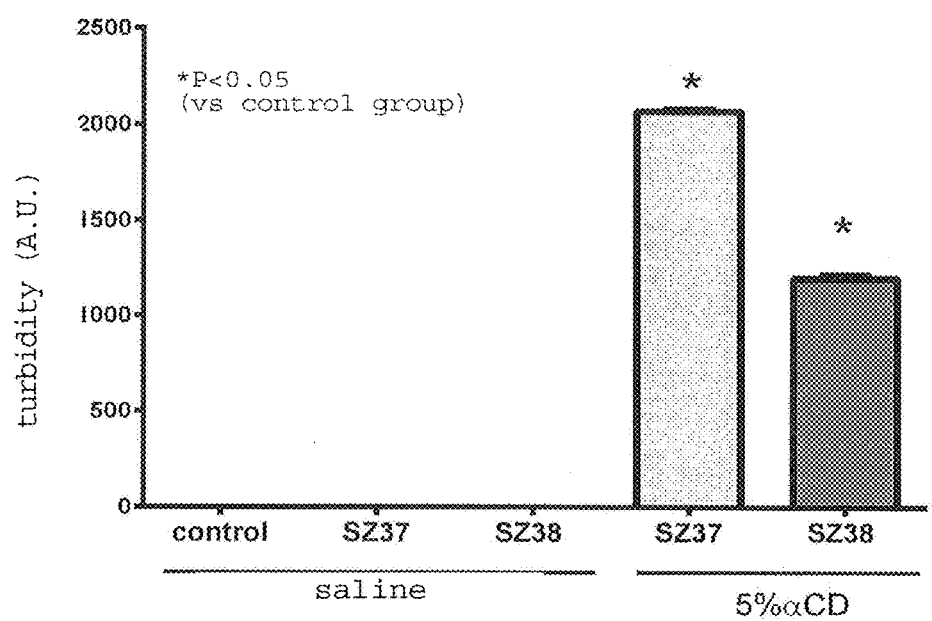
FIG. 11 is a graph showing the results of the dispersibility investigation test of N,N'-bis(2-tetradecylhexadecanoyl)-L-cystine dimethyl ester (SZ37: compound wherein the group corresponding to R³ and R⁴ in the formula (I) is C₂₉ alkyl group) and N,N'-bis(2-octadecyleicosanoyl)-L-cystine dimethyl ester (SZ38: compound wherein the group corresponding to R³ and R⁴ in the formula (I) is C₃₇ alkyl group) in Example 11.
Figure 12:
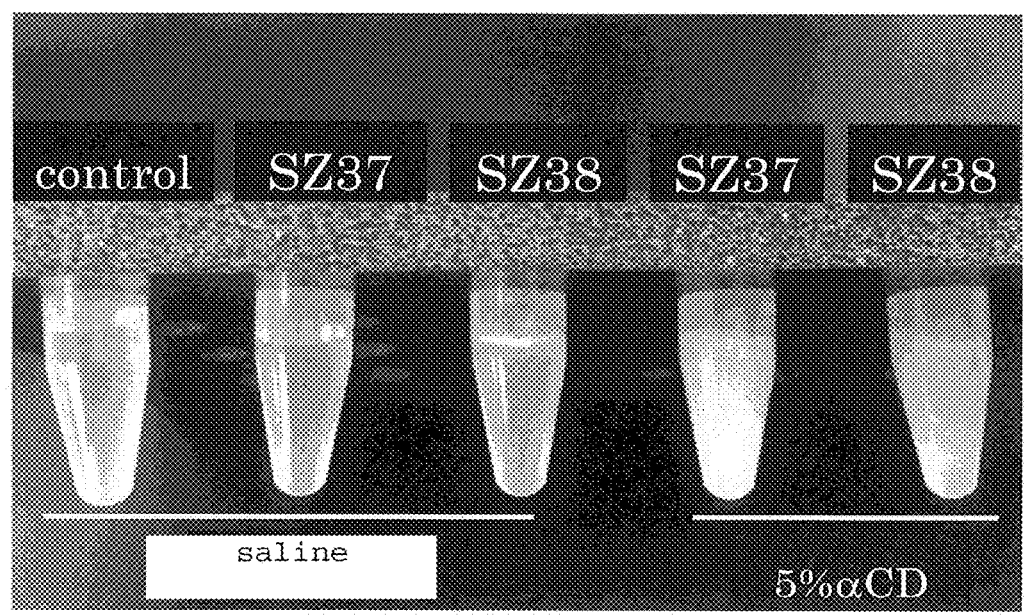
FIG. 12 is a photograph of each stirred sample prepared in Example 11.

The results are shown in FIG. 11. In addition, photographs of respective samples after stirring are shown in FIG. 12.

As is clear from the results shown in FIG. 11, the turbidity of SZ37 and SZ38 dispersed in 5% αCD-added saline was significantly higher than that of SZ37 and SZ38 dispersed in saline. As is clear from the photograph of FIG. 12, it could be confirmed that SZ37 and SZ38 that could not be dispersed in saline could be uniformly dispersed in 5% αCD-added saline.

Example 12

Investigation Test of Dispersion Solvent of N,N'-bis(2-tetradecylhexadecanoyl)-L-cystine dimethyl ester (SZ37) and N,N'-bis(2-octadecyleicosanoyl)-L-cystine dimethyl ester (SZ38)

Whether the dispersion state varies depending on the dispersion solvent when SZ37 and SZ38 are dispersed was studied. In the same manner as in Example 10, SZ37 and SZ38 were added 1% β-cyclodextrin (hereinafter to be also referred to simply as βCD)-added saline or 5% αCD-added saline, and the mixture was stirred. The absorbance (OD Value=650 nm) was measured by a microplate reader, and the turbidity was calculated as an index of dispersibility. The measurement method of turbidity as in Example 11. The results are shown in FIG. 13.

Figure 13:
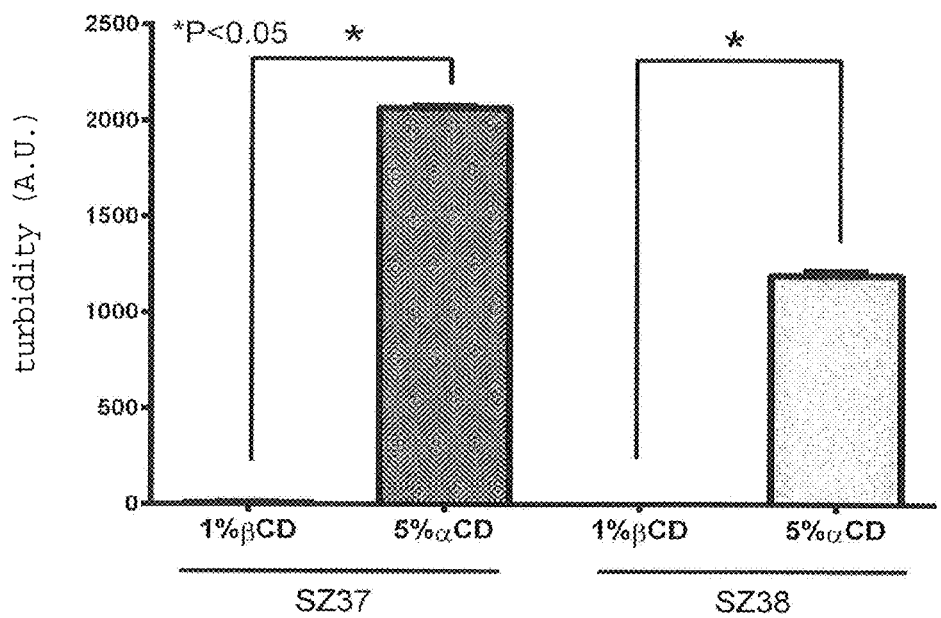
FIG. 13 is a graph showing the results of the investigation test of the dispersion solvents (1% βCD-added saline, 5% αCD-added saline) of N,N'-bis(2-tetradecylhexadecanoyl)-L-cystine dimethyl ester (SZ37: compound wherein the group corresponding to R³ and R⁴ in the formula (I) is C₂₉ alkyl group) and N,N'-bis(2-octadecyleicosanoyl)-L-cystine dimethyl ester (SZ38: compound wherein the group corresponding to R³ and R⁴ in the formula (I) is C₃₇ alkyl group) in Example 12.

As is clear from the results shown in FIG. 13, the turbidity of SZ37 and SZ38 dispersed in 5% αCD-added saline was significantly higher than that of SZ37 and SZ38 dispersed in 1% βCD-added saline. The results show that the dispersibility is higher when 5% αCD-added saline was used rather than 1% βCD-added saline.

(4) Adjuvant Activity Test

Example 13

Evaluation Test of Adjuvant Activity of N,N'-bis(2-tetradecylhexadecanoyl)-L-cystine dimethyl ester (SZ37) and N,N'-bis(2-octadecyleicosanoyl)-L-cystine dimethyl ester (SZ38)

8-Week-old female BALB/c mice were divided into groups (N=6), and each group was primarily immunized by dorsal-subcutaneous administration of (1) ovalbumin (OVA) (10 µg) dissolved in saline as an antigen (OVA single administration group), (2) OVA (10 µg) and, as an adjuvant, N,N'-bis(2-tetradecylhexadecanoyl)-L-cystine dimethyl ester (SZ37) (0.256 µmol) added to saline, (3) OVA (10 µg) and N,N'-bis(2-octadecyleicosanoyl)-L-cystine dimethyl ester (SZ38) (0.256 µmol) added to saline, (4) OVA (10 µg) and SZ37 (0.256 µmol) dissolved or dispersed in 5% αCD-added saline, and (5) OVA (10 µg) and SZ38 (0.256 µmol) dissolved or dispersed in 5% αCD-added saline, each per mouse. One week later, the secondary immunization was carried out by dorsal-subcutaneous administration of solutions or dispersions similar to those of the above-mentioned (1) to (5) again. Two weeks from the secondary immunization, the blood was extracted under anesthesia, and the obtained serum sample was measured for anti OVA-specific IgG1 subclass antibody. The results are shown in FIG. 14.

Figure 14:
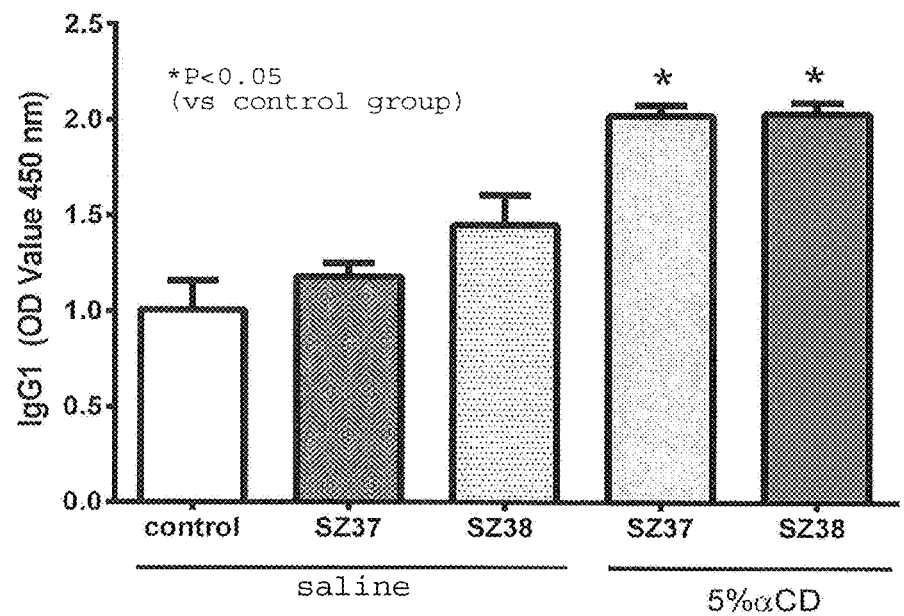
FIG. 14 is a graph showing the results of the evaluation test of adjuvant activity (saline, 5% αCD-added saline) of N,N'-bis(2-tetradecylhexadecanoyl)-L-cystine dimethyl ester (SZ37: compound wherein the group corresponding to R³ and R⁴ in the formula (I) is C₂₉ alkyl group) and N,N'-bis(2-octadecyleicosanoyl)-L-cystine dimethyl ester (SZ38: compound wherein the group corresponding to R³ and R⁴ in the formula (I) is C₃₇ alkyl group) in Example 13, wherein "control" shows OVA single administration group.

As is clear from the results shown in FIG. 14, production of anti OVA-specific IgG1 subclass antibody significantly increased in the group administered with SZ37 and SZ38 dispersed in 5% αCD-added saline, as compared to that of the OVA single administration group (in Figure: control). On the other hand, production of anti OVA-specific IgG1 subclass antibody did not increase significantly in the group administered with SZ37 and SZ38 dispersed in saline as compared that of the OVA single administration group (in Figure: control). The results confirm that N,N'-bis(2-tetradecylhexadecanoyl)-L-cystine dimethyl ester (SZ37) and N,N'-bis(2-octadecyleicosanoyl)-L-cystine dimethyl ester (SZ38) are preferably dispersed in 5% αCD-added saline rather than saline to use them as an adjuvant.

Example 14

Evaluation Test of Adjuvant Activity of N,N'-bis (hexadecanoyl)-L-cystine dimethyl ester (SZ22), N,N'-bis(tridecanoyl)-L-cystine dimethyl ester (SZ34), N,N'-bis(octadecanoyl)-L-cystine dimethyl ester (SZ35) and N,N'-bis(triacontanoyl)-L-cystine dimethyl ester (SZ36)

8-Week-old female BALB/c mice were divided into groups (N=6), and each group was primarily immunized by dorsal-subcutaneous administration of (1) ovalbumin (OVA) (10 μg) dissolved in 5% αCD-added saline as an antigen (OVA single administration group), (2) OVA (10 μg) and N,N'-bis(hexadecanoyl)-L-cystine dimethyl ester (SZ22) (0.256 μmol) dissolved or dispersed in 5% αCD-added saline, (3) OVA (10 μg) and N,N'-bis(tridecanoyl)-L-cystine dimethyl ester (SZ34) (0.256 μmol) dissolved or dispersed in 5% αCD-added saline, (4) OVA (10 μg) and N,N'-bis (octadecanoyl)-L-cystine dimethyl ester (SZ35) (0.256 μmol) dissolved or dispersed in 5% αCD-added saline, and (5) OVA (10 μg) and N,N'-bis(triacontanoyl)-L-cystine dimethyl ester (SZ36) (0.256 μmol) dissolved or dispersed in 5% αCD-added saline, each per mouse. One week later, the secondary immunization was carried out by dorsal-subcutaneous administration of solutions or dispersions similar those of the above-mentioned (1) to (5) again. Two weeks from the secondary immunization, the blood was extracted under anesthesia, and the obtained serum sample was measured for anti OVA-specific IgG1 subclass antibody. The results are shown in FIG. 15.

Figure 15:
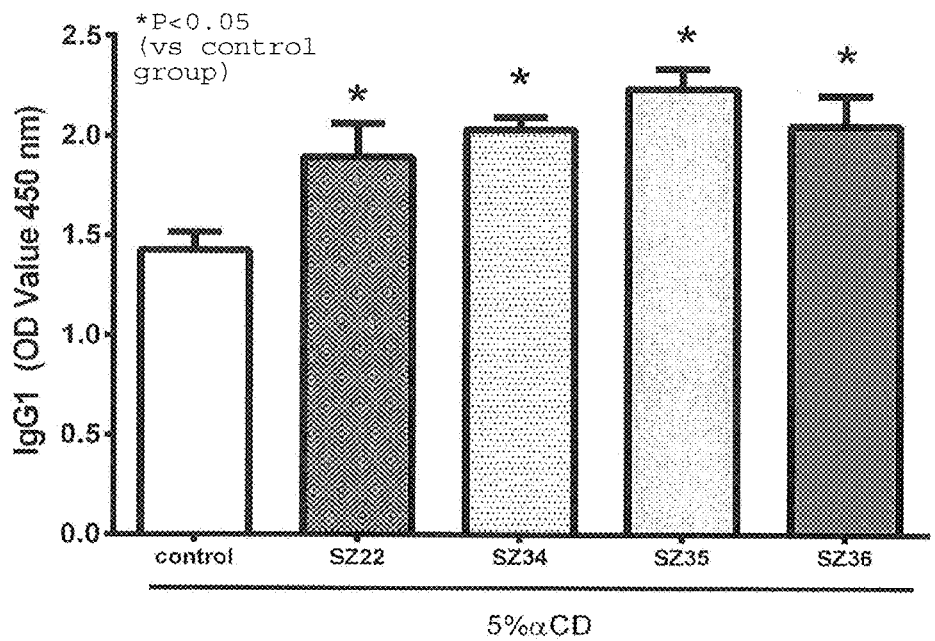
FIG. 15 is a graph showing the results of the evaluation test of adjuvant activity (5% αCD-added saline) of N,N'-bis(hexadecanoyl)-L-cystine dimethyl ester (SZ22: compound wherein the group corresponding to R³ and R⁴ in the formula (I) is C₁₅ alkyl group), N,N'-bis(tridecanoyl)-L-cystine dimethyl ester (SZ34: compound wherein the group corresponding to R³ and R⁴ in the formula (I) is C₁₂ alkyl group), N,N'-bis(octadecanoyl)-L-cystine dimethyl ester (SZ35: compound wherein the group corresponding to R³ and R⁴ in the formula (I) is C₁₇ alkyl group) and N,N'-bis(triacontanoyl)-L-cystine dimethyl ester (SZ36: compound wherein the group corresponding to R³ and R⁴ in the formula (I) is C₂₉ alkyl group) in Example 14, wherein "control" shows OVA single administration group.

As is clear from the results shown in FIG. 15, production of anti OVA-specific IgG1 subclass antibody significantly increased in SZ22, SZ34, SZ35, SZ36 dispersed in 5% αCD-added saline as compared to that of the OVA single administration group (in Figure: control). The results confirm that N,N'-bis(hexadecanoyl)-L-cystine dimethyl ester (SZ22), N,N'-bis(tridecanoyl)-L-cystine dimethyl ester (SZ34), N,N'-bis(octadecanoyl)-L-cystine dimethyl ester (SZ35) and N,N'-bis(triacontanoyl)-L-cystine dimethyl ester (SZ36) dispersed in 5% αCD-added saline also have an adjuvant activity.

Example 15

Evaluation Test of Adjuvant Activity of N,N'-bis(2-heptylundecanoyl)-L-cystine dimethyl ester (SZ23) and N,N'-bis(octadecanoyl)-L-cystine dimethyl ester (SZ35)

8-Week-old female BALB/c mice were divided into groups (N=6), and each group was primarily immunized by dorsal-subcutaneous administration of (1) ovalbumin (OVA) (10 μg) dissolved in 5% αCD-added saline as an antigen (control group), (2) OVA (10 μg) and SZ23 (0.256 μmol) dissolved or dispersed in 5% αCD-added saline, and (3) OVA (10 μg) and SZ35 (0.256 μmol) dissolved or dispersed in 5% αCD-added saline, each per mouse. One week later, the secondary immunization was carried out by dorsal-subcutaneous administration of solutions or dispersions similar to those of the above-mentioned (1) to (3) again. Two weeks from the secondary immunization, the blood was extracted under anesthesia, and the obtained serum sample was measured for anti OVA-specific IgG1 subclass antibody. The results are shown in FIG. 16.

Figure 16:
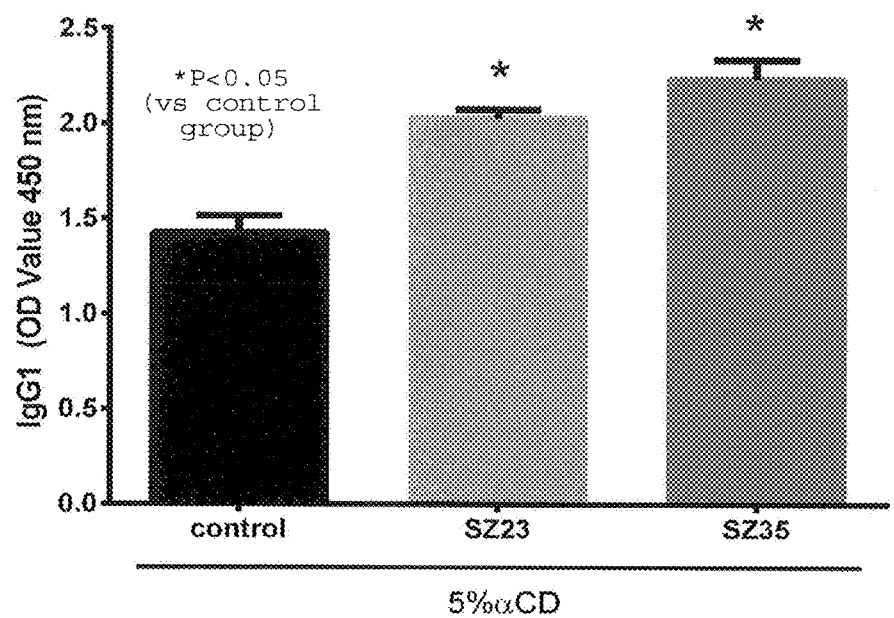
FIG. 16 is a graph showing the results of the evaluation test of adjuvant activity (5% αCD-added saline) of N,N'-bis(2-heptylundecanoyl)-L-cystine dimethyl ester (SZ23: compound wherein the group corresponding to R³ and R⁴ in the formula (I) is C₁₇ alkyl group) and N,N'-bis(octadecanoyl)-L-cystine dimethyl ester (SZ35: compound wherein the group corresponding to R³ and R⁴ in the formula (I) is C₁₇ alkyl group) in Example 15, wherein "control" shows OVA single administration group.

As is clear from the results shown in FIG. 16, production of anti OVA-specific IgG1 subclass antibody significantly increased in SZ23, SZ35 dispersed in 5% αCD-added saline as compared to that of the control group (in Figure: control). The results confirm that N,N'-bis(2-heptylundecanoyl)-L-cystine dimethyl ester (SZ23) dispersed in 5% αCD-added saline also has an adjuvant activity as does N,N'-bis(octadecanoyl)-L-cystine dimethyl ester (SZ35).

Example 16

Evaluation Test of Adjuvant Activity of N,N'-bis (octadecanoyl)-L-cystine dimethyl ester (SZ35) and N,N'-bis(docosaneyl)-L-cystine dimethyl ester (SZ66)

8-Week-old female BALB/c mice were divided into groups (N=6), and each group was primarily immunized by dorsal-subcutaneous administration of (1) ovalbumin (OVA) (10 μg) dissolved in 5% αCD-added saline as an antigen (control group), (2) OVA (10 μg) and SZ35 (0.256 μmol) dissolved or dispersed in 5% αCD-added saline, and (3) OVA (10 μg) and SZ66 (0.256 μmol) dissolved or dispersed in 5% αCD-added saline, each per mouse. One week later, the secondary immunization was carried out by dorsal-subcutaneous administration of solutions or dispersions similar to those of the above-mentioned (1) to (3) again. Two weeks from the secondary immunization, the blood was extracted under anesthesia, and the obtained serum sample was measured for anti OVA-specific IgG1 subclass antibody. The results are shown in FIG. 17.

Figure 17:
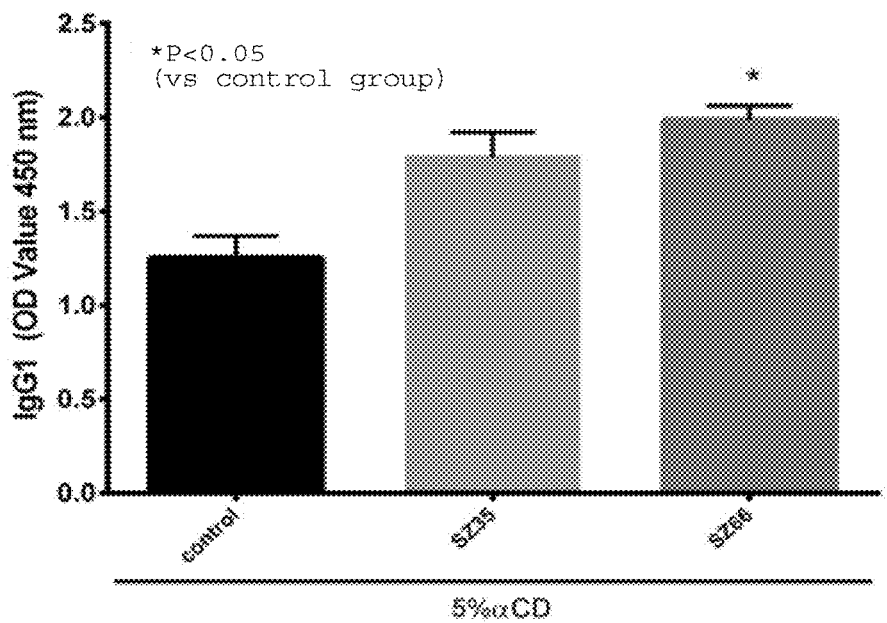
FIG. 17 is a graph showing the results of the evaluation test of adjuvant activity (5% αCD-added saline) of N,N'-bis(octadecanoyl)-L-cystine dimethyl ester (SZ35: compound wherein the group corresponding to R³ and R⁴ in the formula (I) is C₁₇ alkyl group) and N,N'-bis(docosanoyl)-L-cystine dimethyl ester (SZ66: compound wherein the group corresponding to R³ and R⁴ in the formula (I) is C₂₁ alkyl group) in Example 16, wherein "control" shows OVA single administration group.

As is clear from the results shown in FIG. 17, production of anti OVA-specific IgG1 subclass antibody significantly increased in SZ35, SZ66 dispersed in 5% αCD-added saline as compared to that of the control group (in Figure: control). The results confirm that N,N'-bis(docosanoyl)-L-cystine dimethyl ester (SZ66) dispersed in 5% αCD-added saline also has an adjuvant activity.

(5) Evaluation Test as Intranasal Influenza Vaccine Adjuvant

Example 17

Evaluation Test of Adjuvant Activity of Intranasal Influenza Vaccine of N,N'-bis(octadecanoyl)-L-cystine dimethyl ester (SZ35)

8-Week-old female BALB/c mice were divided into groups (N=6), and each group was primarily immunized by intranasal administration of (1) saline, (2) influenza vaccine (Influenza HA Vaccine "SEIKEN", manufactured by Denka Seiken Co. Ltd.) (20 μl) diluted with saline (influenza vaccine single administration group) as an antigen, (3) influenza vaccine (20 μl) and N,N'-bis(octadecanoyl)-L-cystine dimethyl ester (SZ35) (0.55 μg) as an adjuvant diluted with saline, (4) influenza vaccine (20 μl) and N,N'-bis(octadecanoyl)-L-cystine dimethyl ester (SZ35) (1.64 μg) as an adjuvant diluted with saline, and (5) influenza vaccine (20 μl) and N,N'-bis(octadecanoyl)-L-cystine dimethyl ester (SZ35) (4.92 μg) as an adjuvant diluted with saline, each per mouse. Two weeks later, the secondary immunization was carried out by intranasal administration of solutions similar to those of the above-mentioned (1) to (5) again. Two weeks from the secondary immunization, the whole blood was extracted under anesthesia, and nasal cavity washing was performed. The obtained serum samples were measured for anti-influenza IgG1 subclass antibody and HI titer assay (hemagglutination inhibition test) was performed. As a nasal cavity wash, thorax of mouse was opened to expose trachea, the trachea was incised, an Atom venous catheter with clause was inserted and 1 mL of saline was injected. The liquid discharged from the nose was centrifuged at 10000 g for 3 min, and the supernatant was recovered and used as a nasal cavity wash sample. The nasal cavity wash sample was subjected to the measurement of anti-influenza IgA antibody and IgG antibody. The measurement method was as follows.
Measurement Method of Anti-Influenza IgG1 Subclass Antibody, Anti-Influenza IgA Antibody and IgG Antibody 0.5 µg/ml influenza vaccine (Influenza HA Vaccine "SEIKEN", manufactured by Denka Seiken Co. Ltd.) was added to a 96 well plate by 100 µl per well, and the mixture was incubated at 4° C. overnight. After incubation, the mixture was washed three times with 200 µl of PBS-T (PBS+0.05% (v/v) Tween 20) per well, and blocked with 100 µl of 5% FCS/PBS solution per well at room temperature for 1-2 hr. Thereafter, the mixture was washed three times with PBS-T (200 µl/well), a diluted serum sample (100 µl/well), nasal cavity wash sample, and the same amount of 5% FCS/PBS solution as a control was added, and the mixture was incubated at 37° C. for 1 hr. Then, the mixture was washed five times with PBS-T (200 µl/well), a diluted biotinylated anti-mouse IgG1 antibody, an IgA antibody and an IgG antibody (100 µl/well) was added, and the mixture was incubated at 37° C. for 45 min. Then, the mixture was washed five times with PBS-T (200 µl/well), a diluted anti-biotin-HRP antibody was added (100 µl/well), and the mixture was incubated at 37° C. for another 30 min. Thereafter, the mixture was washed five times with PBS-T (200 µl/well), TMB substrate solution was added (100 µl/well), and the mixture was reacted at room temperature for 10 to 15 min. Thereafter, a reaction quenching liquid (2N sulfuric acid solution) was added (50 µl/well) to discontinue a color developing reaction, and the absorbance (OD Value=450 nm) was measured by a microplate reader.
HI Titer Assay This assay was performed according to the protocol of "influenza virus HI reagent "SEIKEN"". To remove non-specific inhibitor in a serum sample, RDE (Receptor Destorying Enzyme, manufactured by Denka Seiken Co. Ltd.) (300 µl) was added to a serum sample and HI antiserum (A/California/7/2009(H1N1), serum control) (100 µl), and the mixture was incubated at 37° C. overnight. The mixture was heated at 56° C. for 60 min to quench the reaction of RDEs, and PBS (600 µl) was added. Thereto was added a chicken red blood cell suspension (50 µl) diluted to 50% and, after sufficient blending, the mixture was left standing at ambient temperature (15° C. to 25° C.) for 60 min. This was centrifuged at 900 g for 5 min, and the supernatant was recovered and used as an HI sample. Then, to determine the HA antigen amount to be used in the HI assay, HA antigen (A/California/7/2009(H1N1)) and chicken red blood cells were mixed as follows. First, 50 µl of HA antigen (A/California/7/2009(H1N1)) diluted 5-fold with PBS was added to a 96 well round-bottomed plate, and PBS (50 µl) was added thereto to give a 10-fold diluted solution. The 10-fold diluted solution was serially diluted 20-fold, 40-fold, 80-fold, 160-fold, 320-fold, 640-fold, 1280-fold with PBS, 50 µl of chicken red blood cell suspension diluted to 0.5% with PBS was added to all these wells, and up to which dilution fold the red blood cells do not precipitate was observed. This time, precipitation was observed at 80-fold dilution, and HA value was 1:80 (80HA/50 µl). Since 4HA/25 µl antigen solution was used in this HI titer assay, the antigen solution was diluted 10-fold and used.

The HI sample (25 µl) adjusted above and diluted 10-fold with PBS was added to a 96 well round-bottomed plate, and used as a 10-fold diluted solution. The 10-fold diluted solution was serially diluted 20-fold, 40-fold, 80-fold, 160-fold, 320-fold, 640-fold, 1280-fold with PBS, 25 µl of HA antigen (A/California/7/2009(H1N1)) was added to all these wells, and the mixture was incubated at room temperature (15° C.-25° C.) for 30 min. Then, precipitation of red blood cell was observed. When precipitation of red blood cell was observed up to 80-fold, the HI antibody value was 80.

Figure 18:
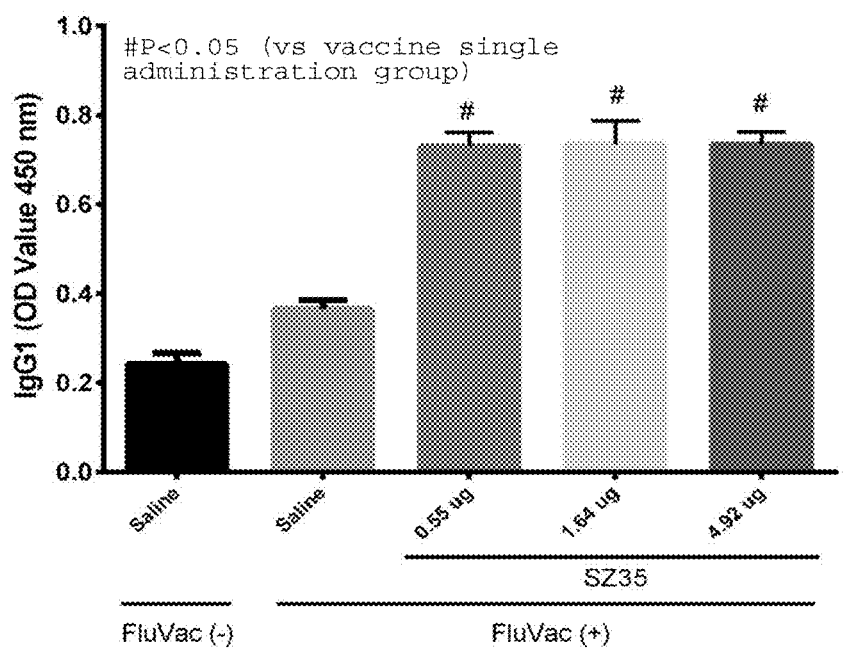
FIG. 18 is a graph showing the results of the evaluation test of IgG1 subclass antibody production by N,N'-bis(octadecanoyl)-L-cystine dimethyl ester (SZ35: compound wherein the group corresponding to R³ and R⁴ in the formula (I) is C₁₇ alkyl group) in a serum sample in intranasal administration of influenza vaccine to mouse in Example 17, wherein "FluVac(−)", "FluVac(+)" show influenza vaccine non-administration group and influenza vaccine administration group, respectively.
Figure 19:
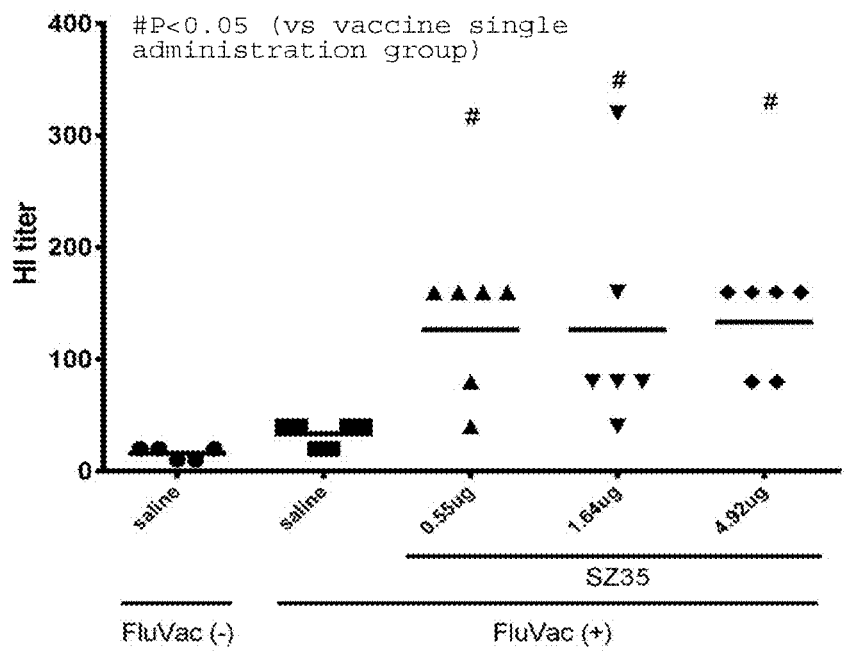
FIG. 19 is a graph showing the results of the HI (Hemagglutinin Inhibition) titer evaluation test (hemagglutination inhibition test) of N,N'-bis(octadecanoyl)-L-cystine dimethyl ester (SZ35: compound wherein the group corresponding to R³ and R⁴ in the formula (I) is C₁₇ alkyl group) in intranasal administration of influenza vaccine to mouse in Example 17, wherein "FluVac(−)", "FluVac(+)" show influenza vaccine non-administration group and influenza vaccine administration group, respectively.
Figure 20:
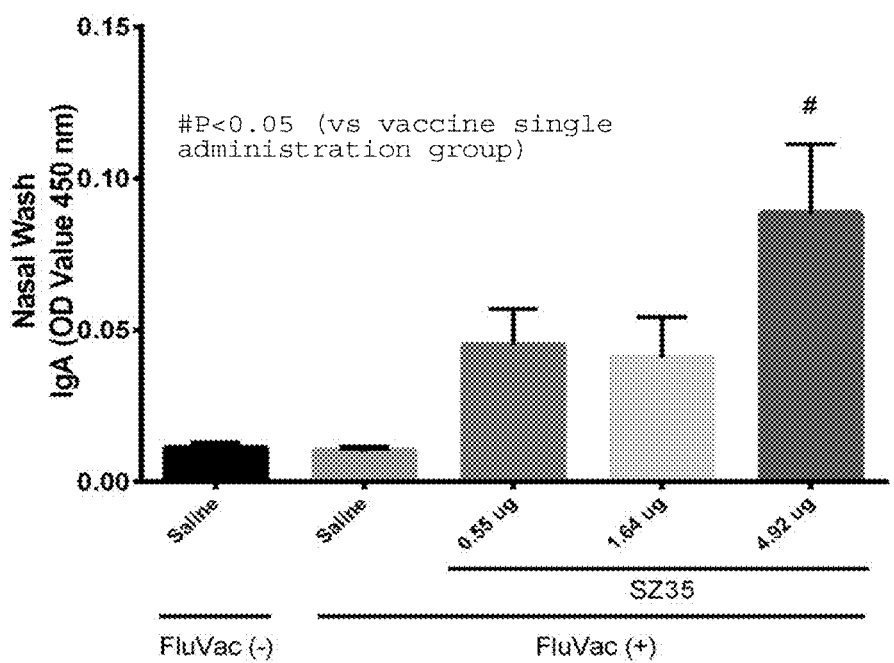
FIG. 20 is a graph showing the results of the evaluation test of IgA antibody production by N,N'-bis(octadecanoyl)-L-cystine dimethyl ester (SZ35: compound wherein the group corresponding to R³ and R⁴ in the formula (I) is C₁₇ alkyl group) in a nasal cavity wash in intranasal administration of influenza vaccine to mouse in Example 17, wherein "FluVac(−)", "FluVac(+)" show influenza vaccine non-administration group and influenza vaccine administration group, respectively.
Figure 21:
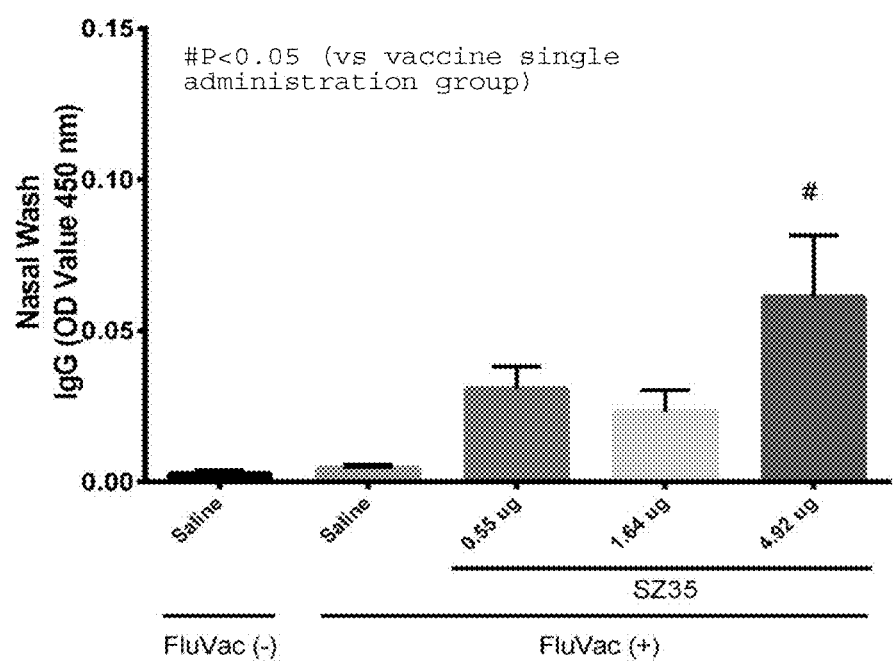
FIG. 21 is a graph showing the results of the evaluation test of IgG antibody production by N,N'-bis(octadecanoyl)-L-cystine dimethyl ester (SZ35: compound wherein the group corresponding to $R^3$ and $R^4$ in the formula (I) is $C_{17}$ alkyl group) in a nasal cavity wash in intranasal administration of influenza vaccine to mouse in Example 17, wherein "FluVac(−)", "FluVac(+)" show influenza vaccine non-administration group and influenza vaccine administration group, respectively.

The evaluation results of IgG1 subclass antibody production in serum sample are shown in FIG. 18, the results of HI titer evaluation test in serum sample are shown in FIG. 19, the evaluation results of IgA antibody production in nasal cavity wash are shown in FIG. 20, and the evaluation results of IgG antibody production in nasal cavity wash are shown in FIG. 21.

As is clear from the results shown in FIG. 18, production of anti-influenza IgG1 subclass antibody in the serum of the SZ35 addition group (in Figure: SZ35 0.55 µg, 1.64 µg, 4.92 µg) significantly increased as compared to that of the influenza vaccine single administration group. The results confirm that N,N'-bis(octadecanoyl)-L-cystine dimethyl ester (SZ35) has an adjuvant activity for influenza vaccine.

As is clear from the results shown in FIG. 19, HI antibody value significantly increase in the serum of the SZ35 addition group (in Figure: SZ35 0.55 µg, 1.64 µg, 4.92 µg) as compared to that of the influenza vaccine single administration group. The results confirm that production of antibody against A/California/7/2009(H1N1), which is an antigen contained in influenza vaccine, is enhanced by the addition of N,N'-bis(octadecanoyl)-L-cystine dimethyl ester (SZ35).

As is clear from the results shown in FIG. 20, production of anti-influenza IgA antibody in the nasal cavity wash of the SZ35 addition group (in Figure: SZ35 4.92 µg) significantly increased as compared to that of the influenza vaccine single administration group. The results confirm that N,N'-bis(octadecanoyl)-L-cystine dimethyl ester (SZ35) is an adjuvant that induces IgA to influenza vaccine on the nasal mucosa of the administration site.

As is clear from the results shown in FIG. 21, production of anti-influenza IgG antibody in the nasal cavity wash of the SZ35 addition group (in Figure: SZ35 4.92 µg) significantly increased as compared to that of the influenza vaccine single administration group. The results confirm that N,N'-bis(octadecanoyl)-L-cystine dimethyl ester (SZ35) is an adjuvant that induces IgG to influenza vaccine on the nasal mucosa of the administration site.

INDUSTRIAL APPLICABILITY

Since the compound of the present invention has an antigen-specific IgG1 antibody production-enhancing effect (immunostimulatory effect), it is useful as an immunostimulating agent. Particularly, since the compound of the present invention has an immunostimulatory effect equivalent to or not less than that of conventional aluminum gel adjuvants, does not induce production of IgE antibody, and scarcely shows problematic allergy inducing activity of conventional aluminum gel adjuvants, it can be an effective and safe adjuvant. Furthermore, since the compound of the present invention induces production of IgA antibody on the mucosa, and potentiates production of blood IgG antibody, it can also be a mucosal vaccine adjuvant of which the research and development are ongoing at present.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An immunostimulating method, comprising administering to a subject in need thereof an effective amount of at least one kind of compound represented by formula (I):

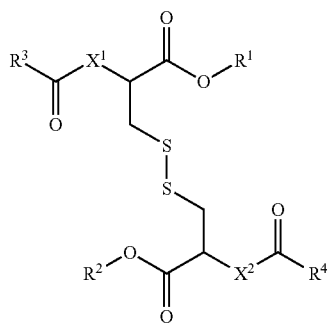

wherein
R$^1$ and R$^2$ are the same or different and each is a C$_{1-6}$ alkyl group;
R$^3$ and R$^4$ are the same or different and each is a C$_{12-37}$ alkyl group;
X$^1$ is —O—, —NR$^5$— wherein R$^5$ is a hydrogen atom or a C$_{1-6}$ alkyl group, or —S—; and
X$^2$ is —O—, —NR$^6$— wherein R$^6$ is a hydrogen atom or a C$_{1-6}$ alkyl group, or —S—.

2. The immunostimulating method according to claim 1, wherein R$^1$ and R$^2$ are each methyl.

3. The immunostimulating method according to claim 1, wherein X$^1$ and X$^2$ are each —NH—.

4. The immunostimulating method according to claim 1, wherein R$^3$ and R$^4$ are the same or different and each is a C$_{12-35}$ alkyl group.

5. The immunostimulating method according to claim 1, wherein R$^3$ and R$^4$ are the same or different and each is a C$_{12-30}$ alkyl group.

6. The immunostimulating method according to claim 1, wherein said compound represented by formula (I) is selected from the group consisting of:
N,N'-bis(hexadecanoyl)-L-cystine dimethyl ester;
N,N'-bis(2-heptylundecanoyl)-L-cystine dimethyl ester;
N,N'-bis[5,7,7-trimethyl-2-(1,3,3-trimethylbutyl)octanoyl]-L-cystine dimethyl ester;
N,N'-bis(tridecanoyl)-L-cystine dimethyl ester;
N,N'-bis(octadecanoyl)-L-cystine dimethyl ester;
N,N'-bis(triacontanoyl)-L-cystine dimethyl ester,
N,N'-bis(2-tetradecylhexadecanoyl)-L-cystine dimethyl ester;
N,N'-bis(2-octadecyleicosanoyl)-L-cystine dimethyl ester; and
N,N'-bis(docosanoyl)-L-cystine dimethyl ester.

7. The immunostimulating method according to claim 1, wherein said compound represented by formula (I) is selected from the group consisting of:
N,N'-bis(hexadecanoyl)-L-cystine dimethyl ester;
N,N'-bis(2-heptylundecanoyl)-L-cystine dimethyl ester;
N,N'-bis[5,7,7-trimethyl-2-(1,3,3-trimethylbutyl)octanoyl]-L-cystine dimethyl ester;
N,N'-bis(tridecanoyl)-L-cystine dimethyl ester;
N,N'-bis(octadecanoyl)-L-cystine dimethyl ester; and
N,N'-bis(triacontanoyl)-L-cystine dimethyl ester.

8. The immunostimulating method according to claim 1, wherein said compound represented by formula (I) is administered in combination with α-cyclodextrin.

9. The immunostimulating method according to claim 1, wherein said compound represented by formula (I) is administered in combination with α-cyclodextrin, and wherein R$^3$ and R$^4$ are the same or different and each is a C$_{29-37}$ alkyl group.

10. The immunostimulating method according to claim 1, wherein said compound represented by formula (I) is an adjuvant.

11. A pharmaceutical composition, comprising:
(a) at least one compound represented by formula (I):

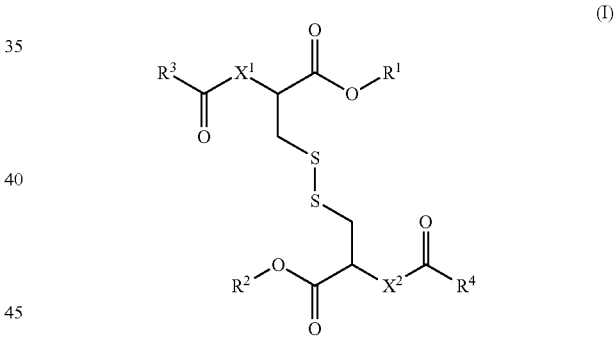

wherein
R$^1$ and R$^2$ are the same or different and each is a C$_{1-6}$ alkyl group;
R$^3$ and R$^4$ are the same or different and each is a C$_{12-37}$ alkyl group;
X$^1$ is —O—, —NR$^5$— wherein R$^5$ is a hydrogen atom or a C$_{1-6}$ alkyl group, or —S—; and
X$^2$ is —O—, —NR$^6$— wherein R$^6$ is a hydrogen atom or a C$_{1-6}$ alkyl group, or —S—; and
(b) α-cyclodextrin.

12. The pharmaceutical composition according to claim 11, wherein R$^1$ and R$^2$ are each methyl.

13. The pharmaceutical composition according to claim 11, wherein X$^1$ and X$^2$ are each —NH—.

14. The pharmaceutical composition according to claim 11, wherein R$^3$ and R$^4$ are the same or different and each is a C$_{29-37}$ alkyl group.

15. The pharmaceutical composition according to claim 11, wherein said compound represented by formula (I) is selected from the group consisting of:

N,N'-bis(hexadecanoyl)-L-cystine dimethyl ester;
N,N'-bis(2-heptylundecanoyl)-L-cystine dimethyl ester;
N,N'-bis[5,7,7-trimethyl-2-(1,3,3-trimethylbutyl)octanoyl]-L-cystine dimethyl ester;
N,N'-bis(tridecanoyl)-L-cystine dimethyl ester;
N,N'-bis(octadecanoyl)-L-cystine dimethyl ester;
N,N'-bis(triacontanoyl)-L-cystine dimethyl ester;
N,N'-bis(2-tetradecylhexadecanoyl)-L-cystine dimethyl ester;
N,N'-bis(2-octadecyleicosanoyl)-L-cystine dimethyl ester; and
N,N'-bis(docosanoyl)-L-cystine dimethyl ester.

16. A compound represented by formula (I):

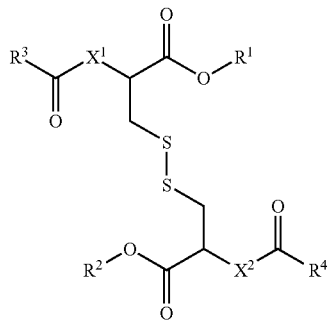

wherein
  $R^1$ and $R^2$ are the same or different and each is a $C_{1-6}$ alkyl group;
  $R^3$ and $R^4$ are the same or different and each is a $C_{12-37}$ alkyl group;
  $X^1$ is —O—, —NR$^5$— wherein $R^5$ is a hydrogen atom or a $C_{1-6}$ alkyl group, or —S—; and
  $X^2$ is —O—, —NR$^6$— wherein $R^6$ is a hydrogen atom or a $C_{1-6}$ alkyl group, or —S—
excluding N,N'-bis(hexadecanoyl)-L-cystine dimethyl ester, N,N'-bis(hexadecanoyl)-L-cystine di-tert-butyl ester, and N,N'-bis(octadecanoyl)-L-cystine dimethyl ester.

17. The compound according to claim 16, wherein $R^1$ and $R^2$ are each methyl.

18. The compound according to claim 16, wherein $X^1$ and $X^2$ are each —NH—.

19. The compound according to claim 16, wherein $R^3$ and $R^4$ are the same or different and each is a $C_{12-35}$ alkyl group.

20. The compound according to claim 16, wherein $R^3$ and $R^4$ are the same or different and each is a $C_{12-30}$ alkyl group.

21. The compound according to claim 16, wherein $R^3$ and $R^4$ are the same or different and each is a $C_{29-37}$ alkyl group.

22. A compound selected from the group consisting of:
N,N'-bis(2-heptylundecanoyl)-L-cystine dimethyl ester;
N,N'-bis[5,7,7-trimethyl-2-(1,3,3-trimethylbutyl)octanoyl]-L-cystine dimethyl ester;
N,N'-bis(tridecanoyl)-L-cystine dimethyl ester;
N,N'-bis(triacontanoyl)-L-cystine dimethyl ester;
N,N'-bis(2-tetradecylhexadecanoyl)-L-cystine dimethyl ester;
N,N'-bis(2-octadecyleicosanoyl)-L-cystine dimethyl ester; and
N,N'-bis(docosanoyl)-L-cystine dimethyl ester.

23. A compound selected from the group consisting of:
N,N'-bis(2-heptylundecanoyl)-L-cystine dimethyl ester;
N,N'-bis[5,7,7-trimethyl-2-(1,3,3-trimethylbutyl)octanoyl]-L-cystine dimethyl ester;
N,N'-bis(tridecanoyl)-L-cystine dimethyl ester; and
N,N'-bis(triacontanoyl)-L-cystine dimethyl ester.

24. A vaccine, comprising:
(a) at least one compound represented by formula (I):

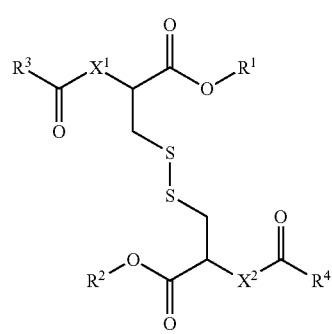

wherein
  $R^1$ and $R^2$ are the same or different and each is a $C_{1-6}$ alkyl group;
  $R^3$ and $R^4$ are the same or different and each is a $C_{12-37}$ alkyl group;
  $X^1$ is —O—, —NR$^5$— wherein $R^5$ is a hydrogen atom or a $C_{1-6}$ alkyl group, or —S—; and
  $X^2$ is —O—, —NR$^6$— wherein $R^6$ is a hydrogen atom or a $C_{1-6}$ alkyl group, or —S—; and
(b) an antigen.

25. The vaccine according to claim 24, wherein $R^1$ and $R^2$ are each methyl.

26. The vaccine according to claim 24, wherein $X^1$ and $X^2$ are each —NH—.

27. The vaccine according to claim 24, wherein $R^3$ and $R^4$ are the same or different and each is a $C_{12-35}$ alkyl group.

28. The vaccine according to claim 24, wherein $R^3$ and $R^4$ are the same or different and each is a $C_{12-30}$ alkyl group.

29. The vaccine according to claim 24, wherein said compound represented by formula (I) is selected from the group consisting of:
N,N'-bis(hexadecanoyl)-L-cystine dimethyl ester;
N,N'-bis(2-heptylundecanoyl)-L-cystine dimethyl ester;
N,N'-bis[5,7,7-trimethyl-2-(1,3,3-trimethylbutyl)octanoyl]-L-cystine dimethyl ester;
N,N'-bis(tridecanoyl)-L-cystine dimethyl ester;
N,N'-bis(octadecanoyl)-L-cystine dimethyl ester;
N,N'-bis(triacontanoyl)-L-cystine dimethyl ester;
N,N'-bis(2-tetradecylhexadecanoyl)-L-cystine dimethyl ester;
N,N'-bis(2-octadecyleicosanoyl)-L-cystine dimethyl ester; and
N,N'-bis(docosanoyl)-L-cystine dimethyl ester.

30. The vaccine according to claim 24, wherein said compound represented by formula (I) is selected from the group consisting of:
N,N'-bis(hexadecanoyl)-L-cystine dimethyl ester;
N,N'-bis(2-heptylundecanoyl)-L-cystine dimethyl ester;
N,N'-bis[5,7,7-trimethyl-2-(1,3,3-trimethylbutyl)octanoyl]-L-cystine dimethyl ester;
N,N'-bis(tridecanoyl)-L-cystine dimethyl ester;
N,N'-bis(octadecanoyl)-L-cystine dimethyl ester; and
N,N'-bis(triacontanoyl)-L-cystine dimethyl ester.

31. A method of vaccination, comprising administering an effective amount of a vaccine according to claim 24 to a subject in need thereof by a route selected from the group consisting of subcutaneous administration and intranasal administration.

* * * * *